US008299216B2

(12) United States Patent
Alani et al.

(10) Patent No.: US 8,299,216 B2
(45) Date of Patent: Oct. 30, 2012

(54) BIOMARKERS FOR MELANOMA

(75) Inventors: Rhoda Myra Alani, Boston, MA (US); Byungwoo Ryu, Boston, MA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/794,832

(22) Filed: Jul. 6, 2007

(65) Prior Publication Data

US 2008/0118462 A1    May 22, 2008

Related U.S. Application Data

(63) Continuation of application No. PCT/US2006/000609, filed on Jan. 9, 2006.

(60) Provisional application No. 60/642,027, filed on Jan. 7, 2005, provisional application No. 60/652,553, filed on Feb. 14, 2005.

(51) Int. Cl.
*C07K 1/00* (2006.01)
(52) U.S. Cl. ..................................... 530/350
(58) Field of Classification Search ........................ None
See application file for complete search history.

(56) References Cited

U.S. PATENT DOCUMENTS

| 2003/0232356 A1 * | 12/2003 | Dooley et al. ............... 435/6 |
| 2004/0121407 A1 * | 6/2004 | Distefano et al. .............. 435/7.1 |
| 2004/0208873 A1 | 10/2004 | Teeling et al. |

FOREIGN PATENT DOCUMENTS

| WO | WO 01/23426 A2 * | 4/2001 |
| WO | WO 01/71355 A2 * | 9/2001 |

OTHER PUBLICATIONS

Tunnacliffe et al (Blood, Jun. 1992, 79(11): abstract).*
Oh et al (Endocrinology, Dec. 1992, 131(6):3123-3125).*
Mondschein et al (Biology of Reproduction, 1991, 44: 315-320).*
Jones et al (Clinical and diagnostic Laboratory Immunology, May 2002, 9(3): 633-638).*
Yang et al (Genome Res., 2001, 11:1888-1898).*
de Wit et al., "Immunohistochemistry in melanocytic proliferative lesions," Histopathology (2004), 44:517-541.
Dhawan et al., "Role of CXCL1 in tumorigenesis of melanoma," Journal of Leukocyte Biology (2002), 72:9-18.
Lazar-Molnar et al., "Autocrine and Paracrine Regulation by Cytokines and Growth Factors in Melanoma," Cytokine (2000), 12(6):547-554.
Payne et al., "The Role of Chemokines in Melanoma Tumor Growth and Metastasis," Journal of Investigative Dermatology (2002), 118(6):915-922.
Richmond et al., "Melanoma Growth Stimulatory Activity: Isolation From Human Melanoma Tumors and Characterization of Tissue Distribution," Journal of Cellular Biochemisry (1998), 36:185-198.
Weterman et al., "Thymosin β-10 Expression in Melanoma Cell Lines and Melanocytic Lesions: A New Progression Marker for Human Cutaneous Melanoma," International Journal of Cancer (1993), 53:278-284.
Yang et al., "Induction of Melanoma in Murine Macrophage Inflammatory Protein 2 Transgenic Mice Heterozygous for Inhibitor of Kinase/Alternate Reading Frame," Cancer Research (2001), 61:8150-8157.
Yang et al., "Constitutive IκB Kinase Activity Correlates with Nuclear Factor-κB Activation in Human Melanoma Cells," Cancer Research (2001), 61:4901-4909.
Database Medline, XP-002580131, Makarova et al., Database Accession No. NLM2477638, Abstract, US National Library of Medicine 1989.
Supplementary European Search Report for related European Application No. EP0671770, dated Jun. 14, 2010.

* cited by examiner

*Primary Examiner* — Sean Aeder
(74) *Attorney, Agent, or Firm* — Edwards Wildman Palmer LLP; Peter F. Corless; Melissa Hunter-Ensor, Esq.

(57) ABSTRACT

The present invention relates to methods of determining melanoma status in a subject. The invention also relates to kits for determining melanoma status in a subject. The invention further relates to methods of identifying biomarker for determining melanoma status in a subject.

10 Claims, 1 Drawing Sheet

BIOMARKERS FOR MELANOMA

RELATED APPLICATIONS

This application claims priority from U.S. Provisional Application Nos. 60/642,027, filed Jan. 7, 2005, 60/652,553, filed Feb. 14, 2005 and which are incorporated herein by reference in their entirety.

BACKGROUND OF THE INVENTION

The incidence of melanoma in the United States has been increasing dramatically over the past several years[1] with melanoma currently being the sixth most common cancer in the United States. Despite the increasing incidence of melanoma, minimal progress has been made in the treatment of advanced stages of this disease, which is notorious for its resistance to chemotherapy and radiotherapy[2]. Presently there are few effective systemic therapies to treat advanced stages of melanoma and the key to improved survival in all affected individuals remains early diagnosis and treatment.

Melanoma is a disease with high metastatic potential even at very early stages of development. There is currently no simple blood test available to readily monitor disease in subjects with a history of melanoma who may be at high risk for recurrent disease or subjects who are high-risk for the development of invasive melanoma. In addition, there are no tests available for evaluation of subject tissue specimens or blood that can predict subject outcome or tumorigenic potential of pigmented lesions of unclear diagnosis.

Multiple studies have shown that there is a high rate of discordance when pathologic specimens of melanocytic lesions are reviewed by multiple pathologists. These changes in diagnosis can have implications in clinical management in up to 40% of subjects who may require further surgical procedures, adjuvant therapy or who may not have needed aggressive surgery. This underlines the need in the art of defining additional tests that may assist in making a histologic diagnosis. In addition, there is a need in the art for the identification of independent predictors of melanoma outcome to allow for identification of subjects most at-risk for developing invasive disease and therefore most in need of aggressive early treatment.

Thus, there is a need in the art for a more thorough understanding of the molecular defects associated with this malignancy and a need for accurate and early diagnosis of melanoma. In present clinical practice, for example, screening for melanoma is based on clinical examination. Current methods for detection, diagnosis, prognosis, and treatment of melanoma fails to satisfactorily reduce the morbidity associated with the disease. There is thus a need in the art for further reduction of mortality rates, and early melanoma detection in minimally invasive, cost efficient formats.

SUMMARY

The present invention provides, for the first time, novel biomarkers that are differentially present in the samples of melanoma subjects and in the samples of control subjects. The present invention also provides sensitive and quick methods and kits that are useful for determining the melanoma status by measuring these novel markers. The measurement of these markers alone or in combination, in subject samples provides information that a diagnostician can correlate with a probable diagnosis of melanoma or a negative diagnosis (e.g., normal or disease-free). The markers are characterized by their known protein identities or by their m/z value or molecular weight and/or by characteristics discussed herein. The markers can be resolved in a sample by using a variety of techniques, e.g., microarrays, PCT techniques (e.g., real time, reverse transcriptase, PCR), and fractionation techniques (e.g., chromatographic separation coupled with mass spectrometry, protein capture using immobilized antibodies or by traditional immunoassays).

The present invention provides a method of qualifying melanoma status in a subject comprising measuring at least one biomarker in a sample from the subject.

In one embodiment, the method of resolution involves Surface-Enhanced Laser Desorption/Ionization ("SELDI") mass spectrometry, in which the surface of the mass spectrometry probe comprises adsorbents that bind the markers.

In one aspect, the invention provides biomarkers for melanoma status comprising one or more of the following Markers 1-104 and combinations thereof. These Markers 1-104 are set forth in Tables 1-3, which follows and are sometimes referred to herein as biomarkers of Table I or similar designations.

In one embodiment, the biomarker for melanoma status of the invention comprises Markers 1-104.

In one embodiment, the method further comprises managing subject treatment based on the status.

TABLE 1

| Marker | Affymetrix Probe ID # | Fold Difference | Gene Description |
|---|---|---|---|
| 1 | 204470_at | 62.26 | GRO1 oncogene (melanoma growth stimulating activity, alpha), CXCL1 |
| 2 | 1555471_a_at | 38.81 | Unknown (protein for MGC: 24252) |
| 3 | 204475_at | 34.21 | matrix metalloproteinase 1 (interstitial collagenase) (MMP1) |
| 4 | 202196_s_at | 24.55 | dickkopf (Xenopus laevis) homolog 3 (DKK3) Human MHC class II HLA-DR-alpha, cell surface glycoprotein |
| 5 | 208894_at | 21.59 | |
| 6 | 211506_s_at | 19.90 | interleukin 8 C-terminal variant (IL8), CXCL8 |
| 7 | 213479_at | 19.73 | neuronal pentraxin II |
| 8 | 212730_at | 17.62 | KIAA0353 protein |
| 9 | 210095_s_at | 17.46 | insulin-like growth factor binding protein 3 |
| 10 | 214247_s_at | 16.68 | regulated in glioma |
| 11 | 206640_x_at | 15.51 | G antigen 7B |
| 12 | 227566_at | 15.20 | neurotrimin |
| 13 | 212143_s_at | 14.90 | insulin-like growth factor binding protein 3 |
| 14 | 212327_at | 14.81 | KIAA1102 protein |
| 15 | 212328_at | 14.21 | KIAA1102 protein |
| 16 | 211776_s_at | 13.33 | Similar to erythrocyte protein band 4.1-like 3 |
| 17 | 206826_at | 13.30 | peripheral myelin protein 2 |
| 18 | 221729_at | 12.66 | collagen, type V, alpha 2 |
| 19 | 226189_at | 12.38 | integrin, beta 8 |
| 20 | 215646_s_at | 12.07 | Homo sapiens versican Vint isoform, mRNA, partial cds |
| 21 | 226847_at | 11.40 | ESTs |
| 22 | 222450_at | 11.34 | TMEPAI, transmembrane, prostate androgen induced |
| 23 | 212942_s_at | 11.19 | KIAA1199 protein |
| 24 | 205207_at | 11.01 | interleukin 6 (interferon, beta 2) |
| 25 | 209619_at | 10.72 | major histocompatibility class II antigen gamma chain |
| 26 | 204619_s_at | 10.34 | chondroitin sulfate proteoglycan 2 (versican) |
| 27 | 211571_s_at | 10.29 | proteoglycan PG-M(V3) |
| 28 | 223614_at | 10.26 | hypothetical protein |
| 29 | 202859_x_at | 10.25 | interleukin 8, CXCL8 |
| 30 | 207030_s_at | 10.01 | cysteine and glycine-rich protein 2 |
| 31 | 229800_at | 9.98 | ESTs |
| 32 | 211538_s_at | 9.94 | heat shock protein |
| 33 | 223638_at | 9.92 | hypothetical protein |
| 34 | 209312_x_at | 9.63 | MHC class II antigen |
| 35 | 205347_s_at | 9.40 | thymosin, beta, identified in neuroblastomacells |
| 36 | 221731_x_at | 8.73 | chondroitin sulfate proteoglycan 2 (versican) |
| 37 | 209774_x_at | 8.63 | cytokine gro-beta, CXCL2 |

TABLE 2

Overexpressed genes in vertical growth phase melanoma (VGP) relative to radial growth phase melanoma (RGP).

| Marker | Affymetirx Probe ID # | Fold Difference | Gene Description | Gene Symbol |
|---|---|---|---|---|
| 38 | 204470_at | 62.26 | chemokine (C-X-C motif) ligand 1 (melanoma growth stimulating activity, alpha) | CXCL1 |
| 39 | 1555471_a_at | 38.81 | formin 2 | FMN2 |
| 40 | 204475_at | 34.21 | matrix metallopeptidase 1 (interstitial collagenase) | MMP1 |
| 41 | 202196_s_at | 24.55 | dickkopf homolog 3 (*Xenopus laevis*) | DKK3 |
| 42 | 208894_at | 21.59 | major histocompatibility complex, class II, DR alpha/// major histocompatibility complex, class II, DR alpha | HLA-DRA |
| 43 | 211506_s_at | 19.90 | interleukin 8 | IL8 |
| 44 | 213479_at | 19.73 | neuronal pentraxin II | NPTX2 |
| 45 | 212730_at | 17.62 | desmuslin | DMN |
| 46 | 210095_s_at | 17.46 | insulin-like growth factor binding protein 3 | IGFBP3 |
| 47 | 214247_s_at | 16.68 | dickkopf homolog 3 (*Xenopus laevis*) | DKK3 |
| 48 | 206640_x_at | 15.51 | G antigen 2 | GAGE2 |
|  |  |  | G antigen 4 | GAGE4 |
|  |  |  | G antigen 5 | GAGE5 |
|  |  |  | G antigen 6 | GAGE6 |
|  |  |  | G antigen 7 | GAGE7 |
|  |  |  | G antigen 7B | GAGE7B |
| 49 | 227566_at | 15.20 | neurotrimin | HNT |
| 50 | 212143_s_at | 14.90 | insulin-like growth factor binding protein 3 | IGFBP3 |
| 51 | 212327_at | 14.81 | KIAA1102 protein | KIAA1102 |
| 52 | 212328_at | 14.21 | KIAA1102 protein | KIAA1102 |
| 53 | 211776_s_at | 13.33 | erythrocyte membrane protein band 4.1-like 3/// erythrocyte membrane protein band 4.1-like 3 | EPB41L3 |
| 54 | 206826_at | 13.30 | peripheral myelin protein 2 | PMP2 |
| 55 | 221729_at | 12.66 | collagen, type V, alpha 2 | COL5A2 |
| 56 | 226189_at | 12.38 | CDNA clone IMAGE: 4794726 | — |
| 57 | 215646_s_at | 12.07 | chondroitin sulfate proteoglycan 2 (versican)/// chondroitin sulfate proteoglycan 2 (versican) | CSPG2 |
| 58 | 226847_at | 11.40 | follistatin | FST |
| 59 | 222450_at | 11.34 | transmembrane, prostate androgen induced RNA | TMEPAI |
| 60 | 212942_s_at | 11.19 | KIAA1199 | KIAA1199 |
| 61 | 205207_at | 11.01 | interleukin 6 (interferon, beta 2) | IL6 |
| 62 | 209619_at | 10.72 | CD74 antigen (invariant polypeptide of major histocompatibility complex, class II antigen-associated) | CD74 |
| 63 | 204619_s_at | 10.34 | chondroitin sulfate proteoglycan 2 (versican) | CSPG2 |
| 64 | 211571_s_at | 10.29 | chondroitin sulfate proteoglycan 2 (versican) | CSPG2 |
| 65 | 223614_at | 10.26 | hypothetical protein DKFZp761D112 | DKFZp761D112 |
| 66 | 202859_x_at | 10.25 | interleukin 8 | IL8 |
| 67 | 207030_s_at | 10.01 | cysteine and glycine-rich protein 2 | CSRP2 |
| 68 | 229800_at | 9.98 | Doublecortin and CaM kinase-like 1 | DCAMKL1 |
| 69 | 211538_s_at | 9.94 | heat shock 70 kDa protein 2 | HSPA2 |
| 70 | 223638_at | 9.92 | hypothetical protein AE2 | AE2 |
| 71 | 209312_x_at | 9.63 | major histocompatibility complex, class II, DR beta 1 - major histocompatibility complex, class II, DR beta 1 | HLA-DRB1 |
| 72 | 205347_s_at | 9.40 | thymosin-like 8 | TMSL8 |
| 73 | 232674_at | 9.27 | urocortin 2 | UCN2 |
| 74 | 1561691_at | 9.02 | hypothetical protein LOC285735 | LOC285735 |
| 75 | 222449_at | 8.87 | transmembrane, prostate androgen induced RNA | TMEPAI |
| 76 | 221731_x_at | 8.73 | chondroitin sulfate proteoglycan 2 (versican) | CSPG2 |
| 77 | 209774_x_at | 8.63 | chemokine (C-X-C motif) ligand 2 | CXCL2 |

TABLE 3

Genes down-regulated in VGP compared to RGP

| Marker | Affymetrix Probe ID # | Fold Difference | Gene Description | Gene Symbol |
|---|---|---|---|---|
| 78 | 1565162_s_at | 218.9 | microsomal glutathione S-transferase 1 | MGST1 |
| 79 | 224918_x_at | 102.7 | microsomal glutathione S-transferase 1 | MGST1 |
| 80 | 202935_s_at | 58.7 | SRY (sex determining region Y)-box 9 (campomelic dysplasia, autosomal sex-reversal) | SOX9 |
| 81 | 213506_at | 46.8 | coagulation factor II (thrombin) receptor-like 1 | F2RL1 |
| 82 | 202936_s_at | 46.5 | SRY (sex determining region Y)-box 9 (campomelic dysplasia, autosomal sex-reversal) | SOX9 |
| 83 | 201015_s_at | 34.3 | junction plakoglobin | JUP |
| 84 | 207076_s_at | 31.9 | argininosuccinate synthetase | ASS |
| 85 | 229404_at | 20 | twist homolog 2 (*Drosophila*) | TWIST2 |

TABLE 3-continued

Genes down-regulated in VGP compared to RGP

| Marker | Affymetrix Probe ID # | Fold Difference | Gene Description | Gene Symbol |
|---|---|---|---|---|
| 86 | 208792_s_at | 19.6 | clusterin (complement lysis inhibitor, SP-40, 40, sulfated glycoprotein 2, testosterone-repressed prostate message 2, apolipoprotein J) | CLU |
| 87 | 206429_at | 17.5 | coagulation factor II (thrombin) receptor-like 1 | F2RL1 |
| 88 | 202391_at | 14.5 | brain abundant, membrane attached signal protein 1 | BASP1 |
| 89 | 204083_s_at | 12.6 | tropomyosin 2 (beta) | TPM2 |
| 90 | 212599_at | 9.8 | autism susceptibility candidate 2 | AUTS2 |
| 91 | 213603_s_at | 9.8 | ras-related C3 botulinum toxin substrate 2 (rho family, small GTP binding protein Rac2) | RAC2 |
| 92 | 229831_at | 8.6 | contactin 3 (plasmacytoma associated) | CNTN3 |
| 93 | 227769_at | 7.7 | G protein-coupled receptor 27 | GPR27 |
| 94 | 229150_at | 7.7 | Melanophilin | MLPH |
| 95 | 228156_at | 7 | *Homo sapiens*, clone IMAGE: 4346533, mRNA | — |
| 96 | 212316_at | 6.9 | nucleoporin 210 kDa | NUP210 |
| 97 | 226682_at | 6.5 | hypothetical protein LOC283666 | LOC283666 |
| 98 | 228570_at | 5.8 | BTB (POZ) domain containing 11 | BTBD11 |
| 99 | 202283_at | 5.6 | serpin peptidase inhibitor, clade F (alpha-2 antiplasmin, pigment epithelium derived factor), member 1 | SERPINF1 |
| 100 | 209735_at | 5.5 | ATP-binding cassette, sub-family G (WHITE), member 2 | ABCG2 |
| 101 | 1554544_a_at | 5.3 | myelin basic protein | MBP |
| 102 | 238332_at | 5.3 | ankyrin repeat domain 29 | ANKRD29 |
| 103 | 231859_at | 5.2 | chromosome 14 open reading frame 132 | C14orf132 |
| 104 | 223322_at | 5.1 | Ras association (RalGDS/AF-6) domain family 5 | RASSF5 |

In one embodiment, Markers 78-104 are down-regulated in melanoma subjects.

In one embodiment, Markers 1-77 are up-regulated in melanoma subjects.

In another embodiment, the biomarker is Marker 1. In a related embodiment, the biomarker comprises Markers 1, 6, 24, and 37; 38, 43, 61 and 77; 1 and 6; 1 and 24; 1 and 37; 6 and 24; 6 and 37; or 24 and 37

In one aspect, the invention provides methods of qualifying melanoma status in a subject comprising measuring at least one biomarker in a sample from the subject, wherein the biomarker is selected from one or more of the biomarkers of Tables 1-3, and correlating the measurement with melanoma status.

In one embodiment, the melanoma is in one or more of radial growth phase, early vertical growth phase, late vertical growth phase, or metastatic melanoma.

In another embodiment, managing subject treatment is selected from ordering further diagnostic tests, administering at least one therapeutic agent, surgery, surgery followed or preceded by administering at least one therapeutic agent, biotherapy, and taking no further action.

In another embodiment, the therapeutic agent is selected from one or more of fotemustine, dacarbazine, interferon, cisplatin, tamoxifen, interleukin-2, ifn alfa, vinblastin, orcannubris, or vaccine.

In one embodiment, the method may further comprise measuring the at least one biomarker after subject management.

In one embodiment, the melanoma status is selected from one or more of the presence, absence or amount of one or more of biomarkers 1-104.

In one embodiment, the method may further comprise assessing the status of the melanoma.

In one embodiment, the melanoma status is assessed by one or more of visual examination, tissue sample examination, subject's symptoms, or evaluation of blood chemistry.

In another embodiment, the marker is detected by one or more of mass spectrometry, PCR, or microarray analysis.

In another embodiment, the biomarker is detected by SELDI.

In another embodiment, the sample from the subject is one or more of blood, blood plasma, serum, urine, cells, organs, seminal fluids, bone marrow, saliva, stool, a cellular extract, a tissue sample, a tissue biopsy, or cerebrospinal fluid.

In another embodiment, biomarkers are protein markers and are measured by immunoassay.

In another embodiment, at least two biomarkers are measured.

In another embodiment, at least three biomarkers are measured.

In another embodiment, measuring is selected from detecting the presence or absence of the biomarkers(s), quantifying the amount of marker(s), and qualifying the type of biomarker.

In one embodiment, the method further comprises communicating a diagnosis to a subject, wherein the diagnosis results from the correlation of the biomarkers of Tables 1-3 with melanoma.

Provided herein, according to one aspect, are methods for identifying a candidate compound for treating melanoma comprising contacting one or more of the biomarkers of Tables 1-3 with a test compound; and determining whether the test compound interacts with the biomarker, wherein a compound that interacts with the biomarker is identified as a candidate compound for treating melanoma.

Provided herein, according to one aspect, are methods of treating melanoma comprising administering to a subject suffering from or at risk of developing melanoma a therapeutically effective amount of a compound capable of modulating the expression or activity of one or more of the biomarkers of Table 1.

Provided herein, according to one aspect, are methods of treating a condition in a subject comprising administering to a subject a therapeutically effective amount of a compound which modulates the expression or activity of one or more of the biomarkers of Tables 1-3.

In one embodiment, the compound is selected from the group consisting of enzyme inhibitors, cytotoxic drugs, cytokins, chemokines, antibodies, a DNA molecule, an RNA molecule, a small molecule, a peptide, and a peptidomimetic.

In another embodiment, the at least one biomarker is measured by immunoassay.

In one embodiment, the correlation is performed by a software classification algorithm.

Provided herein, according to one aspect, are methods for identifying a melanoma treatment, comprising contacting a cell with a test compound, measuring at least one biomarker, wherein the biomarker is selected from one or more of the biomarkers of Tables 1-3, and correlating the measurement with a determination of efficacy.

In one embodiment, the cell is one or more of is one or more of a radial-growth phase line (WM35, SBC12, WM1552C), an early vertical-growth phase line (WM1341D), a late vertical growth phase line (WM902B, WM278, WM983A), a metastatic melanoma line (WM852, WM983B, 1205Lu), or primary human melanocytes.

Provided herein, according to one aspect, are methods of determining the melanoma status of a subject, comprising obtaining a biomarker profile from a sample taken from the subject; and comparing the subject's biomarker profile to a reference biomarker profile obtained from a reference population, wherein the comparison is capable of classifying the subject as belonging to or not belonging to the reference population; wherein the subject's biomarker profile and the reference biomarker profile comprise one or more markers listed in Table 1.

In one embodiment, the methods may further comprise repeating the method at least once, wherein the subject's biomarker profile is obtained from a separate sample taken each time the method is repeated.

In one embodiment, samples from the subject are taken about 24 hours apart.

In another embodiment, the comparison of the biomarker profiles can determine melanoma status in the subject with an accuracy of at least about 60% to about 99%.

In one embodiment, the reference biomarker profile is obtained from a population comprising a single subject, at least two subjects, and at least 20 subjects.

Provided herein, according to one aspect, are methods for the identification of a therapeutic target for melanoma comprising comparing an expression profile of a melanoma cell with an expression profile of one a reference cell, wherein the comparison is capable of classifying proteins or transcripts in the profile as being associated with invasion.

In another embodiment, the melanoma cell is one or more of a blood cell from a melanoma subject, a tissue sample from a melanoma subject or a melanoma cell line.

In one embodiment, the melanoma cell line is one or more of a radial-growth phase line, an early vertical-growth phase line, or a metastatic melanoma line. In one embodiment, the cell is one or more of is one or more of a radial-growth phase line (WM35, SBC12, WM1552C), an early vertical-growth phase line (WM1341D), a late vertical growth phase line (WM902B, WM278, WM983A), or a metastatic melanoma line (WM852, WM983B, 1205Lu).

In one embodiment, the methods may further comprise identifying a candidate compound that interacts with the identified therapeutic target.

In one embodiment, identifying the candidate compound comprises contacting the identified target with a test compound and determining whether the test compound interacts with the identified target, wherein a compound that interacts with the biomarker is identified as a candidate compound for treating melanoma Provided herein, according to one aspect are purified biomolecule selected from the biomarkers of Tables 1-3.

Provided herein, according to one aspect are kits for aiding the diagnosis of melanoma, comprising an adsorbent, wherein the adsorbent retains one or more biomarkers selected from one or more of the markers of Table 1, and written instructions for use of the kit for detection of melanoma.

In one embodiment, the instructions provide for contacting a test sample with the adsorbent and detecting one or more biomarkers retained by the adsorbent.

In another embodiment, the adsorbent is an antibody, single or double stranded oligonucleotide, amino acid, protein, peptide or fragments thereof.

In one embodiment, one or more protein biomarkers is detected using mass spectrometry, immunoassays, or PCR.

Markers of the invention may be detected, for example, by mass spectrometry according to one embodiment. In a related embodiment, the markers are detected by SELDI. In another related embodiment, the marker or markers are detected by capturing the marker on a biochip having a hydrophobic surface and detecting the captured marker by SELDI. Suitable biochips include the IMAC3 ProteinChip® Array and the WCX2 ProteinChip® Array. In another related embodiment, markers are detected by nucleic acid arrays, e.g., DNA arrays or by PCR methods.

In one embodiment, the methods for qualifying melanoma status in a subject further comprise generating data on immobilized subject samples on a biochip, by subjecting the biochip to laser ionization and detecting intensity of signal for mass/charge ratio; and transforming the data into computer readable form; executing an algorithm that classifies the data according to user input parameters, for detecting signals that represent biomarkers present in melanoma subjects and are lacking in non-melanoma subject controls.

In one embodiment, one or more of the biomarkers are detected using laser desorption/ionization mass spectrometry, comprising providing a probe adapted for use with a mass spectrometer comprising an adsorbent attached thereto; contacting the subject sample with the adsorbent; desorbing and ionizing the biomarker or biomarkers from the probe; and detecting the desorbed/ionized markers with the mass spectrometer.

In one embodiment, least one or more protein biomarkers are detected using immunoassays.

In one embodiment, the sample from the subject is one or more of blood, blood plasma, serum, urine, cells, organs, seminal fluids, bone marrow, saliva, stool, a cellular extract, a tissue sample, a tissue biopsy, and cerebrospinal fluid.

In one embodiment, the methods for qualifying melanoma status in a subject further comprise measuring the amount of each biomarker in the subject sample and determining the ratio of the amounts between the markers. In a related embodiment, the measuring is selected from detecting the presence or absence of the biomarkers(s), quantifying the amount of marker(s), and qualifying the type of biomarker. In one embodiment, at least two biomarkers are measured. In a related embodiment, at least three biomarkers are measured. In another embodiment, at least four biomarkers are measured.

In one embodiment, the protein biomarkers are measured by one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS).sup.n, atmospheric pressure photoionization mass spectrometry (APPI-MS), APPI-MS/MS, and APPI-(MS)$_n$, quadrupole mass spectrometry, fourier transform mass spectrometry (FTMS), and ion trap mass spectrometry, where n is an integer greater than zero.

In one embodiment, the correlating is performed by a software classification algorithm.

The invention provides kits, for example, for aiding the diagnosis of melanoma or the diagnosis of the subtypes of melanoma. The kits may suitably include an adsorbent, wherein the adsorbent retains one or more biomarkers selected from one or more of the markers of Tables 1-3, and written instructions for use of the kit for detection of melanoma.

In one embodiment, the kit for aiding the diagnosis of the subtypes of melanoma, comprises an adsorbent, wherein the adsorbent retains one or more biomarkers selected from each of Markers 1-37, and written instructions for use of the kit for detection of the melanoma or a subtype of melanoma, e.g., superficial spreading, nodular, acrolentiginous, and lentigo maligna.

Kits may also comprise instructions provide for contacting a test sample with the adsorbent and detecting one or more biomarkers retained by the adsorbent, wherein the adsorbent is, for example, an antibody, single or double stranded oligonucleotide, amino acid, protein, peptide or fragments thereof.

In one embodiment, the one or more protein biomarkers is detected using mass spectrometry, immunoassays, or PCR. In another embodiment, the measuring is selected from detecting the presence or absence of the biomarkers(s), quantifying the amount of marker(s), and qualifying the type of biomarker.

In one aspect, the invention provides methods for identifying a candidate compound for treating melanoma comprising contacting one or more of the biomarkers of Tables 1-3 with a test compound; and determining whether the test compound interacts with the biomarker, wherein a compound that interacts with the biomarker is identified as a candidate compound for treating melanoma.

The invention also provides methods of treating melanoma comprising administering to a subject suffering from or at risk of developing melanoma a therapeutically effective amount of a compound capable of modulating the expression or activity of one or more of the biomarkers of Tables 1-3. In another aspect, the invention provides methods of treating a condition in a subject comprising administering to a subject a therapeutically effective amount of a compound which modulates the expression or activity of one or more of the biomarkers of Tables 1-3.

In certain embodiments, the compound are selected from the group consisting of enzyme inhibitor, cytotoxic drug, cytokin, chemokine, antibodies, a DNA molecule, an RNA molecule, a small molecule, a peptide, and a peptidomimetic. Classes of drugs include, anti-inflammatory, antibiotic, antiviral, antidepressant, anticonvulsant therapeutics.

According to one aspect, the invention provides methods for modulating the concentration of a biomarker, wherein the biomarker is one or more of the biomarkers listed in Tables 1-3. The method comprises contacting a cell with a test compound, measuring at least one biomarker, wherein the biomarker is selected from one or more of the biomarkers of Tables 1-3, and correlating the measurement with a determination of efficacy.

The invention also provides, in one aspect, a method of identifying a biomarker comprising obtaining an endoscopic sample from a subject, isolating nucleic acid from the sample, analyzing the nucleic acid and correlating the results. The results may be analyzed against a control database of melanoma samples and/or controls.

The invention also provides methods of determining the melanoma status of a subject, comprising (a) obtaining a biomarker profile from a sample taken from the subject; and (b) comparing the subject's biomarker profile to a reference biomarker profile obtained from a reference population, wherein the comparison is capable of classifying the subject as belonging to or not belonging to the reference population; wherein the subject's biomarker profile and the reference biomarker profile comprise one or more markers listed in Tables 1-3.

In one embodiment, the comparison of the biomarker profiles can determine melanoma status in the subject with an accuracy of at least about 60%, 70%, 80%, 90% or approaching 100%.

In certain embodiments, the sample is fractionated by one or more of chemical extraction partitioning, ion exchange chromatography, reverse phase liquid chromatography, isoelectric focusing, one-dimensional polyacrylamide gel electrophoresis (PAGE), two-dimensional polyacrylamide gel electrophoresis (2D-PAGE), thin-layer chromatography, gas chromatography, liquid chromatography, and any combination thereof.

In other methods, the measuring step comprises quantifying the amount of marker(s) in the sample. In other methods, the measuring step comprises qualifying the type of biomarker in the sample.

When the identity of a markers is not yet known, the biomarkers may be sufficiently characterized by, e.g., sequencing methods, antibody methods, nucleic acid methods, mass and by affinity characteristics. It is noted that molecular weight and binding properties are characteristic properties of the markers and not limitations on means of detection or isolation. Furthermore, using the methods described herein or other methods known in the art, the absolute identity of markers can be determined.

The present invention also relates to biomarkers designated as Markers 1-104. Biomarkers of the invention can be characterized in one or more of several respects. In particular, in one aspect, these markers are characterized by molecular weights under the conditions specified herein, particularly as determined by mass spectral analysis. In another aspect, the markers can be characterized by features of the markers' mass spectral signature such as size (including area) and/or shape of the markers' spectral peaks, features including proximity, size and shape of neighboring peaks, etc. In yet another aspect, the markers can be characterized by affinity binding characteristics, particularly ability to binding to cation-exchange and/or hydrophobic surfaces. In preferred embodiments, markers of the invention may be characterized by each of such aspects, i.e. molecular weight, mass spectral signature and cation and/or hydrophobic absorbent binding.

Accuracy and resolution variances associated with the techniques described herein are reflected in the use of the term "about" in the disclosure.

In a preferred embodiment, the present invention provides for a method for detecting and diagnosing (including e.g., differentiating between) different subtypes of melanoma, wherein the method comprises using a biochip array for detecting at least one biomarker in a subject sample; evaluating at least one biomarker in a subject sample, and correlating the detection of one or more protein biomarkers with a melanoma subtype, e.g., superficial spreading, nodular, acrolentiginous, and lentigo maligna.

The biomarkers of the invention may be detected in samples of blood, blood plasma, serum, urine, tissue, cells, organs, seminal fluids, bone marrow, and cerebrospinal fluid.

Preferred detection methods include use of a biochip array. Biochip arrays useful in the invention include protein and nucleic acid arrays. One or more markers are captured on the biochip array and subjected to laser ionization to detect the molecular weight of the markers. Analysis of the markers is, for example, by molecular weight of the one or more markers against a threshold intensity that is normalized against total ion current.

In preferred methods of the present invention, the step of correlating the measurement of the biomarkers with melanoma status is performed by a software classification algorithm. Preferably, data is generated on immobilized subject samples on a biochip array, by subjecting the biochip array to laser ionization and detecting intensity of signal for mass/charge ratio; and transforming the data into computer readable form; and executing an algorithm that classifies the data according to user input parameters, for detecting signals that represent markers present in melanoma subjects and are lacking in non-melanoma subject controls.

Preferably the biochip surfaces are, for example, ionic, anionic, hydrophobic; comprised of immobilized nickel or copper ions; comprised of a mixture of positive and negative ions; and/or comprised of one or more antibodies, single or double stranded nucleic acids, proteins, peptides or fragments thereof, amino acid probes, or phage display libraries.

In other preferred methods one or more of the markers are measured using laser desorption/ionization mass spectrometry, comprising providing a probe adapted for use with a mass spectrometer comprising an adsorbent attached thereto, and contacting the subject sample with the adsorbent, and desorbing and ionizing the marker or markers from the probe and detecting the deionized/ionized markers with the mass spectrometer.

Preferably, the laser desorption/ionization mass spectrometry comprises: providing a substrate comprising an adsorbent attached thereto; contacting the subject sample with the adsorbent; placing the substrate on a probe adapted for use with a mass spectrometer comprising an adsorbent attached thereto; and desorbing and ionizing the marker or markers from the probe and detecting the desorbed/ionized marker or markers with the mass spectrometer.

The adsorbent can for example be, hydrophobic, hydrophilic, ionic or metal chelate adsorbent, such as nickel or copper, or an antibody, single- or double stranded oligonucleotide, amino acid, protein, peptide or fragments thereof.

In another embodiment, a process for purification of a biomarker, comprising fractioning a sample comprising one or more protein biomarkers by size-exclusion chromatography and collecting a fraction that includes the one or more biomarker; and/or fractionating a sample comprising the one or more biomarkers by anion exchange chromatography and collecting a fraction that includes the one or more biomarkers. Fractionation is monitored for purity on normal phase and immobilized nickel arrays. Generating data on immobilized marker fractions on an array is accomplished by subjecting the array to laser ionization and detecting intensity of signal for mass/charge ratio; and transforming the data into computer readable form; and executing an algorithm that classifies the data according to user input parameters, for detecting signals that represent markers present in melanoma subjects and are lacking in non-melanoma subject controls. Preferably fractions are subjected to gel electrophoresis and correlated with data generated by mass spectrometry. In one aspect, gel bands representative of potential markers are excised and subjected to enzymatic treatment and are applied to biochip arrays for peptide mapping.

In another aspect one or more biomarkers are selected from gel bands representing Markers 1-104 described herein.

Purified proteins for detection of melanoma and/or screening and aiding in the diagnosis of melanoma and/or generation of antibodies for further diagnostic assays are provided.

In further embodiments, the invention provides methods for identifying compounds (e.g., antibodies, nucleic acid molecules (e.g., DNA, RNA), small molecules, peptides, and/or peptidomimetics) capable of treating melanoma comprising contacting at least one or more of a biomarker selected from Markers 1-104, and combinations thereof with a test compound; and determining whether the test compound interacts with, binds to, or modulates the biomarker, wherein a compound that interacts with, binds to, or modulates the biomarker is identifies as a compound capable of treated melanoma.

In another embodiment, the invention provides methods of treating melanoma comprising administering to a subject suffering from or at risk of developing melanoma a therapeutically effective amount of a compound (e.g., an antibody, nucleic acid molecule (e.g., DNA, RNA), small molecule, peptide, and/or peptidomimetic) capable of modulating the expression or activity of one or more of the Biomarkers 1-104.

In one aspect, the invention provides methods of determining the melanoma status of a subject, comprising (a) obtaining a biomarker profile from a sample taken from the subject; and (b) comparing the subject's biomarker profile to a reference biomarker profile obtained from a reference population, wherein the comparison is capable of classifying the subject as belonging to or not belonging to the reference population; wherein the subject's biomarker profile and the reference biomarker profile comprise one or more markers listed in Tables 1-3.

Methods of the invention, one embodiment, may further comprise repeating the method at least once, wherein the subject's biomarker profile is obtained from a separate sample taken each time the method is repeated.

In another embodiment, samples from the subject are taken about 24, 30, 48, 60, and/or 72 hours apart.

In another embodiment, the comparison of the biomarker profiles can determine melanoma status in the subject with an accuracy of at least about 60% to about 99%.

In one embodiment, the reference biomarker profile is obtained from a population comprising a single subject, at least two subjects, and at least 20 subjects.

Thus, the methods of the present invention provide and solve the need for methods of accurately assessing, i.e., diagnostically, prognostically, and therapeutically, melanoma.

Other embodiments of the invention are disclosed infra.

DETAILED DESCRIPTION

Figure 1A:
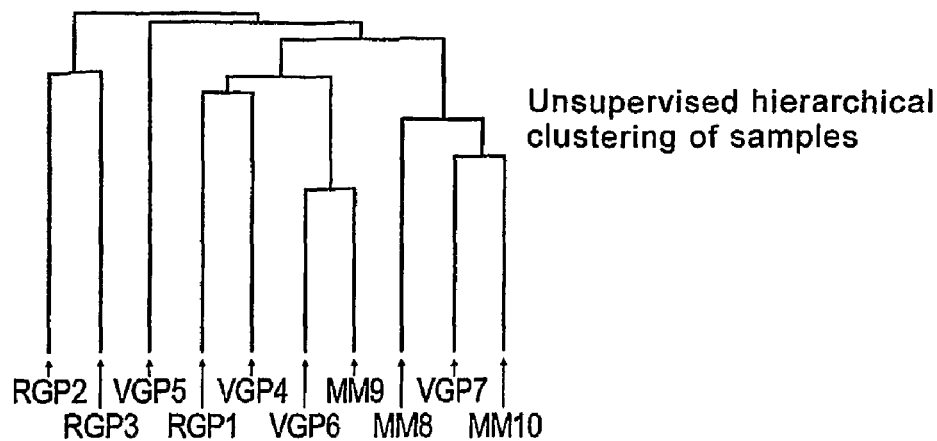
FIG. 1 depicts unsupervised hierarchical clustering of the various stages of melanoma cell lines (A) and paired analysis of gene expression in radial growth phase (RGP) versus vertical growth phase (VGP) and metastatic melanoma (MM) (B).

The present invention provides biomarkers generated from comparison of expression profiles from subjects diagnosed with melanoma and from subjects without known neoplastic diseases, using molecular biological techniques and mass spectrometry techniques. In particular, the invention provides that these biomarkers, used individually, or preferably in combination with other biomarkers from this group or with other diagnostic tests, provide a novel method of determining melanoma status in a subject.

The present invention presents markers that are differentially present in samples of melanoma subjects and control subjects, and the application of this discovery in methods and kits for determining melanoma status. These biomarkers are found in samples from melanoma subjects at levels that are different than the levels in samples from subject in whom human melanoma is undetectable. Accordingly, the amount of one or more markers found in a test sample compared to a control, or the presence or absence of one or more markers in the test sample provides useful information regarding the melanoma status of the subject.

The present invention also relates to a method for identification of biomarkers for melanoma, with high specificity and sensitivity. In particular, a panel of biomarkers were identified that are associated with melanoma status.

In accordance with one embodiment of the invention, a series of genes whose expression correlates with melanoma progression and invasion were identified. Preferred up-regulated melanoma progression markers are secreted proteins detectable in circulating blood, e.g., markers 1-77. These secreted biomarkers are useful as a gauge of disease onset/progression in subjects having routine health screenings, routine melanoma screenings, in those suspected of having melanoma, for those with known previous diagnosis of melanoma, and in subjects at high risk for the development of melanoma. In one embodiment, these are known as melanoma "invasion-specific genes." The invasion specific genes are also useful as novel therapeutic targets.

Markers may also be down-regulated in blood or tissue of melanoma subjects compared to controls or reference samples, e.g., Markers 78-104. These markers as useful for the determination of melanoma status in a subject. Markers 78-104 are also useful in distinguishing between stages of melanoma, e.g., between VGP and RGP. That is Markers 78-104 are down-regulation in VGP as compared to RGP and thus, up-regulated in RGP as compared to VGP.

In one embodiment, the identified melanoma biomarkers are useful to predict disease progression. In one embodiment, subjects having a history of melanoma who are at high risk for disease recurrence may be monitored for disease using the instant blood test or other tests described herein. Current disease monitoring is through the use of frequent physical examinations in conjunction with various imaging modalities including CT-scanning, MRI scanning, and PET scanning. Such subject monitoring techniques often detect only grossly-detectable disease which is often difficult to treat. The claimed methods allow for earlier detection of disease recurrence/progression and therefore earlier treatment of subjects with recurrent/progressive disease.

In addition, knowledge of genetic changes that occur in melanoma enable the design and screening for targeted therapeutic agents that interact with the targets. The interaction may be direct or indirect. Theraputic agents are agents that improve survival in subjects with disease, including advanced disease.

Provided herein are in vitro melanoma model systems and microarray technologies to identify molecular and genetic defects associated with melanoma onset or progression and useful diagnostic and prognostic markers for this disease. Such markers are useful clinically to determine therapeutic strategies for subjects and guide subject treatment.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The term "melanoma status" refers to the status of the disease in the subject. Examples of types of melanoma statuses include, but are not limited to, the subject's risk of melanoma, the presence or absence of disease, the stage of disease in a subject (e.g., stages 0-IV and recurrent melanoma), and the effectiveness of treatment of disease. Other statuses and degrees of each status are known in the art.

As used herein, "invasion-specific genes" refers to those genes that are up-regulated or down-regulated in invasive melanomas which are the only melanomas that can become lethal. These invasion specific genes are useful as biomarkers for melanoma and as potential drug targets for treating melanoma. That is the "invasion-specific" will be useful diagnostic markers of melanoma and will be useful predictors of disease outcome (prognostic markers). In addition, secreted tumor markers can be readily detected in subjects serum and will be used as markers of disease status and outcome.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer that uses laser energy as a means to desorb, volatilize, and ionize an analyte.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector—magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of-flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionucleotides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the energy delivered per unit area of interrogated image. A high fluence source, such as a laser, will deliver about 1 mJ/mm2 to 50 mJ/mm2. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (1) electrons that ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Solid support" refers to a solid material which can be derivatized with, or otherwise attached to, a capture reagent. Exemplary solid supports include probes, microtiter plates and chromatographic resins.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

"Surface-Enhanced Affinity Capture" or "SEAC" is a version of SELDI that involves the use of probes comprising an absorbent surface (a "SEAC probe"). "Adsorbent surface" refers to a surface to which is bound an adsorbent (also called a "capture reagent" or an "affinity reagent"). An adsorbent is any material capable of binding an analyte (e.g., a target polypeptide or nucleic acid). "Chromatographic adsorbent" refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047 (Hutchens and Yip, "Use of retentate chromatography to generate difference maps," May 1, 2001).

In some embodiments, a SEAC probe is provided as a pre-activated surface which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Adsorption" refers to detectable non-covalent binding of an analyte to an adsorbent or capture reagent.

"Surface-Enhanced Neat Desorption" or "SEND" is a version of SELDI that involves the use of probes comprising energy absorbing molecules chemically bound to the probe surface. ("SEND probe.") "Energy absorbing molecules" ("EAM") refer to molecules that are capable of absorbing energy from a laser desorption/ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. SEND is further described in U.S. Pat. No. 5,719,060 and U.S. patent application 60/408,255, filed Sep. 4, 2002 (Kitagawa, "Monomers And Polymers Having Energy Absorbing Moieties Of Use In Desorption/Ionization Of Analytes").

"Surface-Enhanced Photolabile Attachment and Release" or "SEPAR" is a version of SELDI that involves the use of probes having moieties attached to the surface that can covalently bind an analyte, and then release the analyte through breaking a photolabile bond in the moiety after exposure to light, e.g., laser light. SEPAR is further described in U.S. Pat. No. 5,719,060.

"Eluant" or "wash solution" refers to an agent, typically a solution, which is used to affect or modify adsorption of an analyte to an adsorbent surface and/or remove unbound materials from the surface. The elution characteristics of an eluant can depend on, for example, pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed.

"Molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Monitoring" refers to observing and/or recording changes in a continuously varying parameter.

"Biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes.

"Protein biochip" refers to a biochip adapted for the capture of polypeptides. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000). Protein biochips produced by Ciphergen Biosystems comprise surfaces having chromatographic or biospecific adsorbents attached thereto at addressable locations. Biochips are farther described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application US20030032043A1 (Pohl and Papanu, "Latex Based Adsorbent Chip," Jul. 16, 2002) and U.S. patent application 60/350,110 (Um et al., "Hydrophobic Surface Chip," Nov. 8, 2001).

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

"Marker" or "biomarker" in the context of the present invention refer to a polypeptide (of a particular apparent molecular weight) or nucleic acid, which is differentially present in a sample taken from subjects having human melanoma as compared to a comparable sample taken from control subjects (e.g., a person with a negative diagnosis or undetectable melanoma, normal or healthy subject). The term "biomarker" is used interchangeably with the term "marker." The biomarkers are identified by, for example, molecular mass in Daltons, and include the masses centered around the identified molecular masses for each marker, affinity binding, nucleic acid detection, etc.

The term "measuring" means methods which include detecting the presence or absence of marker(s) in the sample, quantifying the amount of marker(s) in the sample, and/or qualifying the type of biomarker. Measuring can be accomplished by methods known in the art and those further described herein, including but not limited to microarray analysis (with Significance Analysis of Microarrays (SAM) software), SELDI and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy.

"Detect" refers to identifying the presence, absence or amount of the object to be detected.

The phrase "differentially present" refers to differences in the quantity and/or the frequency of a marker present in a sample taken from subjects having melanoma as compared to a control subject or a reference subject or sample. For example, some markers described herein are present at an elevated level in samples of subjects compared to samples from control subjects, e.g., Markers 1-37 and 38-77. In contrast, other markers described herein are present at a decreased level in samples of melanoma subjects compared to samples from control subjects, e.g., Markers 78-104. Furthermore, a marker can be a polypeptide or a nucleic acid, which is detected at a higher frequency or at a lower frequency in samples of human melanoma subjects compared to samples of control subjects.

Furthermore, a marker can be a polypeptide, which is detected at a higher frequency or at a lower frequency in samples of unaffected tissue from melanoma subjects compared to samples affected tissue from melanoma subjects.

Furthermore, a marker can be a polypeptide, which is detected at a higher frequency or at a lower frequency in samples of human unaffected tissue from melanoma subjects compared to samples of control subjects.

Furthermore, a marker can be a polypeptide, which is detected at a higher frequency or at a lower frequency in samples of human affected tissue from melanoma subjects compared to samples of control subjects.

A marker can be differentially present in terms of quantity, frequency or both.

"Affected tissue," as used herein refers to tissue from a melanoma subject that is grossly diseased tissue (e.g., skin (epidermis and/or dermis) lymph nodes, metastatic sites, e.g., brain, lung, bone, liver, skin) or melanocytes).

"Unaffected tissue," as used herein refers to a tissue from an melanoma subject that is from a portion of tissue that does not have gross disease present, for example tissue that is about 1, 2, 5, 10, 20 or more cm from grossly diseased tissue.

A polypeptide is differentially present between two samples if the amount of the polypeptide or nucleic acid in one sample is statistically significantly different from the amount of the polypeptide or nucleic acid in the other sample. For example, a polypeptide or nucleic acid is differentially present between the two samples if it is present at least about 25%, at least about 50%, at least about 75%, at least about 100%, 120%, at least about 130%, at least about 150%, at least about 180%, at least about 200%, at least about 300%/0, at least about 500%, at least about 700%, at least about 900%, or at least about 1000% greater than it is present in the other sample, or if it is detectable in one sample and not detectable in the other.

Alternatively or additionally, a polypeptide or nucleic acid is differentially present between two sets of samples if the frequency of detecting the polypeptide or nucleic acid in the melanoma subjects' samples is statistically significantly higher or lower than in the control samples. For example, a polypeptide or nucleic acid is differentially present between the two sets of samples if it is detected at least about 25%, at least about 50%, at least about 75%, at least about 100%, at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition, i.e., melanoma. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., μg/ml) or a relative amount (e.g., relative intensity of signals).

A "diagnostic amount" of a marker refers to an amount of a marker in a subject's sample that is consistent with a diagnosis of melanoma. A diagnostic amount can be either in absolute amount (e.g., μg/ml) or a relative amount (e.g., relative intensity of signals).

A "control amount" of a marker can be any amount or a range of amount, which is to be compared against a test amount of a marker. For example, a control amount of a marker can be the amount of a marker in a person without melanoma. A control amount can be either in absolute amount (e.g., μg/ml) or a relative amount (e.g., relative intensity of signals).

As used herein, the term "sensitivity" is the percentage of subjects with a particular disease. For example, in the melanoma group, the biomarkers of the invention have a sensitivity of about 80.0%-98.6%, and preferably a sensitivity of 85%, 87.5%, 90%, 92.5%, 95%, 97%, 98%, 99% or approaching 100%.

As used herein, the term "specificity" is the percentage of subjects correctly identified as having a particular disease i.e., normal or healthy subjects. For example, the specificity is calculated as the number of subjects with a particular disease as compared to non-melanoma subjects (e.g., normal healthy subjects). The specificity of the assays described herein may range from about 80% to 100%. Preferably the specificity is about 90%, 95%, or 100%.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Immunoassay" is an assay that uses an antibody to specifically bind an antigen (e.g., a marker). The immunoassay is characterized by the use of specific binding properties of a particular antibody to isolate, target, and/or quantify the antigen.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well-characterized fragments produced by digestion with various peptidases. This includes, e.g., Fab-" and F(ab)-"$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Managing subject treatment" refers to the behavior of the subject, clinician or physician subsequent to the determination of melanoma status. For example, if the result of the methods of the present invention is inconclusive or there is reason that confirmation of status is necessary, the physician may order more tests. Alternatively, if the status indicates that treatment is appropriate, the physician may schedule the subject for treatment, e.g., surgery, administer one or more therapeutic agents or radiation. Likewise, if the status is negative, e.g., late stage melanoma or if the status is acute, no further action may be warranted. Furthermore, if the results show that treatment has been successful, a maintenance therapy or no further management may be necessary.

Description of the Biomarkers

Melanoma Biomarkers

Melanoma biomarkers include the biomarkers listed in Tables 1. The sequences of these biomarkers may be found by reference to the Affymetrix reference number and primers for amplifying the biomarkers may be developed by those of skill in the art. Seventy seven (77) genes are elevated in most melanoma profiles and most likely contribute towards separation of melanoma from normal controls. These genes include those listed in Tables 1-2, and include genes encoding cytokines, chemokines, growth factors, heat shock proteins, transcription factors, MHC molecules, adhesion molecules. Twenty six (26) genes are down-regulated in most melanoma profiles and most likely contribute towards separation of melanoma from normal controls. These genes include those listed in Table 3, and include genes encoding glutathione S-transferase, amino acid production genes, coagulation factors, G protein coupled receptors, and myelin basic protein.

Further biomarkers for melanoma include the proteins or their encoding nucleic acids for the following pathways or cellular processes: melanocyte differentiation, cellular proliferation, melanin biosynthesis. Chemokines are small protein molecules, ranging in size from 70-130 amino acids. These inducible cytokines are secreted from myeloid, lymphoid and epidermal cells as well as platelets and tumor cells[1]. Originally, chemokines were demonstrated to influence leukocyte activation and migration, initiating the inflammatory/wound healing cascade (Baggiolini M. Chemokines and leukocyte traffic. Nature. 1998; 392(6676):565-568). The chemokines are divided into four classes based on the arrangement of the first 2 (out of 4 total) conserved cysteine residues: C, CC, CXC and CX3C (Baggiolini). The CXC chemokines predominantly act on neutrophils and lymphocytes (Balkwill F, Mantovani A. Inflammation and cancer: Back to Virchow? Lancet. 2001; 357(9255):539-545). CXC chemokines also play a role in the regulation of angiogenesis. Those containing a Glu-Leu-Arg (ELR) motif at the amino terminus promote angiogenesis, while those without the motif are angiostatic (Strieter R M, Polverini P J, Kunkel S L, et al. The functional role of the ELR motif in CXC chemokine-mediated angiogenesis. J Biol Chem. 1995; 270(45): 27348-27357; Yoneda J, Kuniyasu H, Crispens M A, Price J E, Bucana C D, Fidler I J. Expression of angiogenesis-related genes and progression of human ovarian carcinomas in nude mice. J Natl Cancer Inst. 1998; 90(6):447-454; and Huang M, Wang J, Lee P, et al. Human non-small cell lung cancer cells express a type 2 cytokine pattern. Cancer Res. 1995; 55(17): 3847-3853). Examples of CXC chemokines possessing the ELR motif include CXCL1, 2, 3, 5, 6, 7 and CXCL8 (IL-8). CXCL1 is also known as melanocyte growth stimulatory activity (MGSA) or growth-related oncogene-α (gro-α).

Chemokines exert their effects via seven transmembrane G-protein-coupled cell surface receptors. Chemokines may bind multiple different receptors, thus activating the receptors and producing different effects. CXCL1 primarily binds and activates CXCR2, present on neutrophils, monocytes, mast cells, melanocytes, and some CD8+ cells and CD56+NK cells (Amiri K I, Richmond A. Fine tuning the transcriptional regulation of the CXCL1 chemokine. Prog Nucleic Acid Res Mol Biol. 2003; 74:1-36). This interaction of CXCL1 and CXCR2 has been shown to modulate inflammation, angiogenesis, tumorigenesis, wound healing and cell motility (Haghnegahdar H, Du J, Wang D, et al. The tumorigenic and angiogenic effects of MGSA/GRO proteins in melanoma. J Leukoc Biol. 2000; 67(1):53-62; Owen J D, Strieter R, Burdick M, et al. Enhanced tumor-forming capacity for immortalized melanocytes expressing melanoma growth stimulatory activity/growth-regulated cytokine beta and gamma proteins. Int J. Cancer. 1997; 73(1):94-103; and Devalaraja R M, Nanney L B, Du J, et al. Delayed wound healing in CXCR2 knockout mice. J Invest Dermatol. 2000; 115(2): 234-244). It has been proposed that the up-regulation of chemokines, specifically CXCL1 and CXCL8, is due to constitutive activation of the NF-κB pathway (Dhawan P, Richmond A. Role of CXCL1 in tumorigenesis of melanoma. J Leukoc Biol. 2002; 72(1):9-18).

In the cardiovascular realm, CXCL1 serum levels have been evaluated in patients affected by strokes or congestive heart failure (Damas J K, Gullestad L, Ueland T, et al. CXC-chemokines, a new group of cytokines in congestive heart failure-possible role of platelets and monocytes. Cardiovasc Res. 2000; 45(2):428-436; and Losy J, Zaremba J, Skrobanski P. CXCL1 (GRO-alpha) chemokine in acute ischaemic stroke patients. Folia Neuropathol. 2005; 43(2):97-102). In ischemic strokes, there were no appreciable differences in serum CXCL1 levels. However, CSF levels of CXCL1 were elevated in the stroke patients compared with controls and did appear to correlate with size of infarct. Damas et al demonstrated elevated serum levels of IL-8, (CXCL8), gro-α (CXCL1) and epithelial neutrophils activating peptide (ENA)-78 in patients with congestive heart failure. With progressive New York Heart Association (NYHA) class, there was a direct correlation with extent of IL-8 and gro-α level elevation.

CXCL1 is not stored intracellularly; rather its expression is regulated at the transcriptional level (Amiri K I, Richmond A. Fine tuning the transcriptional regulation of the CXCL1 chemokine. Prog Nucleic Acid Res Mol Biol. 2003; 74:1-36). Expression is felt to modulated by inducible transcription factors, for example NF-κB. Upon induction, CXCL1 is expressed and secreted by leukocytes and other tissue cells, including melanoma cells (Dhawan P, Richmond A. Role of CXCL1 in tumorigenesis of melanoma. J Leukoc Biol. 2002; 72(1):9-18). Additionally, CXCL1 production and release from activated platelets has been documented. The contribution of CXCL1 secretion from activated platelets and monocytes has been explored in the setting of CHF (Damas J K, Gullestad L, Ueland T, et al. CXC-chemokines, a new group of cytokines in congestive heart failure-possible role of platelets and monocytes. Cardiovasc Res. 2000; 45(2):428-436). As platelet activation may occur upon blood collection, technique is important to determine an accurate serum level of CXCL1. Thus, any method which would minimize shearing and turbulence should preserve the integrity of the platelets and not effect CXCL1 release.

Melanoma Growth Stimulatory Activity (MGSA) was originally isolated from the media of Hs294Tcells, a human melanoma cell line (Richmond A, Thomas HG. Melanoma growth stimulatory activity: Isolation from human melanoma tumors and characterization of tissue distribution. J Cell Biochem. 1988; 36(2):185-198). MGSA was described as the product of the growth-related oncogene locus (Anisowicz A, Bardwell L, Sager R. Constitutive overexpression of a growth-regulated gene in transformed Chinese hamster and human cells. Proc Natl Acad Sci USA. 1987; 84(20):7188-7192; and Richmond A, Balentien E, Thomas H G, et al. Molecular characterization and chromosomal mapping of melanoma growth stimulatory activity, a growth factor structurally related to beta-thromboglobulin. EMBO J. 1988; 7(7): 2025-2033). It was determined that these correlated with the CXCL1-3 genes cluster on chromosome 4q12-q13 (Zlotnik A, Yoshie O. Chemokines: A new classification system and their role in immunity. Immunity. 2000; 12(2): 121-127). In several aspects, CXCL1 is a therapeutic target and a biomarker for melanoma. The screening assays described herein are useful for identifying therapeutic agents to interact with CXCL1.

Corresponding proteins or fragments of proteins for these biomarkers may be represented as intensity peaks in SELDI (surface enhanced laser desorption/ionization) protein chip/mass spectra with molecular masses centered around the values. As discussed above, Markers 1-104 also may be characterized based on affinity for an adsorbent, particularly binding to a cation-exchange or hydrophobic surface under the conditions specified in the Examples, which follow.

The above-identified biomarkers, are examples of biomarkers, as determined by identity, identified by the methods of the invention and serve merely as an illustrative example and are not meant to limit the invention in any way.

A major advantage of identification of these markers is their high specificity and ability to differentiate between different melanoma states (e.g., between stages 0, I-IV and recurrent melanoma). For example, the biomarkers listed in Tables 2 and 3 are useful to differentiate between vertical growth phase melanoma (VGP) relative to radial growth phase melanoma (RGP). For example, the Table 2 biomarkers are up-regulated in VGP relative to RGP and the biomarkers of Table 3 are down-regulated in VGP compared to RGP. Thus, the level or expression or amount of any one or a combination of these biomarkers is useful in discriminating between VGP and RGP.

More specifically, the present invention is based upon the discovery of markers that are differentially present in samples of human melanoma subjects and control subjects, and the application of this discovery in methods and kits for aiding a melanoma diagnosis. Some of these markers are found at an elevated level and/or more frequently in samples from human melanoma subjects compared to a control (e.g., subjects with diseases other than melanoma). Accordingly, the amount of one or more markers found in a test sample compared to a control, or the mere detection of one or more markers in the test sample provides useful information regarding probability of whether a subject being tested has melanoma or not, and/or whether a subject being tested has a particular melanoma subtype or not.

The proteins and nucleic acids of the present invention have a number of other uses. For example, the markers can be used to screen for compounds that modulate the expression of the markers in vitro or in vivo, which compounds in turn may be useful in treating or preventing human melanoma in subjects. In another example, markers can be used to monitor responses to certain treatments of human melanoma. In yet another example, the markers can be used in heredity studies. For instance, certain markers may be genetically linked. This can be determined by, e.g., analyzing samples from a population of human melanoma subjects whose families have a history of melanoma. The results can then be compared with data obtained from, e.g., melanoma subjects whose families do not have a history of melanoma. The markers that are genetically linked may be used as a tool to determine if a subject whose family has a history of melanoma is pre-disposed to having melanoma.

In another aspect, the invention provides methods for detecting markers which are differentially present in the samples of an melanoma subject and a control (e.g., subjects in non-melanoma subjects). The markers can be detected in a number of biological samples. The sample is preferably a biological biopsy sample or a blood sample.

Any suitable methods can be used to detect one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy. Methods may further include, by one or more of microarrays, PCR methods, electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$_n$, quadrupole mass spectrometry, fourier transform mass spectrometry (FTMS), and ion trap mass spectrometry, where n is an integer greater than zero.

The following example is illustrative of the methods used to identify biomarkers for detection of melanoma. It is not meant to limit or construe the invention in any way. A sample, such as for example, serum from a subject or subject, is immobilized on a biochip. Preferably, the biochip comprises a functionalized, cross-linked polymer in the form of a hydrogel physically attached to the surface of the biochip or covalently attached through a silane to the surface of the biochip. However, any biochip which can bind samples from subjects can be used. The surfaces of the biochips are comprised of, for example, hydrophilic adsorbent to capture hydrophilic proteins (e.g. silicon oxide); carboimidizole functional groups that can react with groups on proteins for covalent binding; epoxide functional groups for covalent binding with proteins (e.g. antibodies, receptors, lectins, heparin, Protein A, biotin/streptavidin and the like); anionic exchange groups; cation exchange groups; metal chelators and the like.

Preferably, samples are pre-fractionated prior to immobilization as discussed below. Analytes or samples captured on the surface of a biochip can be detected by any method known in the art. This includes, for example, mass spectrometry, fluorescence, surface plasmon resonance, ellipsometry and atomic force microscopy. Mass spectrometry, and particularly SELDI mass spectrometry, is a particularly useful method for detection of the biomarkers of this invention. Other methods include, chemical extraction partitioning, ion exchange chromatography, reverse phase liquid chromatography, isoelectric focusing, one-dimensional polyacrylamide gel electrophoresis (PAGE), two-dimensional polyacrylamide gel electrophoresis (2D-PAGE), thin-layer chromatography, gas chromatography, liquid chromatography, and any combination thereof.

Immobilized samples or analytes are preferably subjected to laser ionization and the intensity of signal for mass/charge ratio is detected. The data obtained from the mass/charge ratio signal is transformed into data which is read by any type of computer. An algorithm is executed by the computer user that classifies the data according to user input parameters for detecting signals that represent biomarkers present in, for example, melanoma subjects and are lacking in non-melanoma subject controls. The biomarkers are most preferably identified by their molecular weights.

Test Samples

Subject Types

Samples are collected from subjects to establish melanoma status. The subjects may be subjects who have been determined to have a high risk of melanoma based on their family history, a previous treatment, subjects with physical symptoms known to be associated with melanoma, subjects identified through screening assays (e.g., routine melanoma screening) or other techniques. Other subjects include subjects who have melanoma and the test is being used to determine the effectiveness of therapy or treatment they are receiving. Also, subjects could include healthy people who are having a test as part of a routine examination, or to establish baseline levels of the biomarkers. Samples may be collected from subjects who had been diagnosed with melanoma and received treatment to eliminate the melanoma, or perhaps are in remission. As used herein, "melanoma biopsy" refers to tissue from suspected melanoma, tissue from the edges of suspected melanoma or from normal tissue.

Types of Sample and Preparation of the Sample

The markers can be measured in different types of biological samples. The sample is preferably a biological tissue or fluid sample. Examples of biological tissue sample is a blood or biopsy sample, from for example a melanoma biopsy. Examples of a biological fluid sample useful in this invention include blood, blood serum, plasma, vaginal secretions, urine, tears, saliva, urine, tissue, cells, organs, seminal fluids, bone marrow, cerebrospinal fluid, etc. Because the markers are found in blood and melanoma biopsy, these are preferred sample sources for embodiments of the invention.

Nucleic acids may be obtained from the samples in many ways known to one of skill in the art. For example, extraction methods, including for example, solvent extraction, affinity purification and centrifugation. Selective precipitation may also purify nucleic acids. Chromatography methods may also be utilized including, gel filtration, ion exchange, selective adsorption, or affinity binding. The nucleic acids may be, for example, RNA, DNA or may be synthesized into cDNA. The nucleic acids may be detected using microarray techniques that are well known in the art, for example, Affymetrix arrays followed by multi-dimensional scaling techniques. See R. Ekins and F. W. Chu, Microarrays: their origins and applications. Trends in Biotechnology, 1999, 17, 217-218; D. D. Shoemaker, et al., Experimental annotation of the human genome using microarray technology, Nature Volume 409 Number 6822 Page 922-927 (2001) and U.S. Pat. No. 5,750,015.

The markers can be resolved in a sample by using a variety of techniques, e.g., nucleic acid chips, PCR, real time PCR, reverse transcriptase PCR, real time reverse transcriptase PCR, in situ PCR, chromatographic separation coupled with mass spectrometry, protein capture using immobilized antibodies or by traditional immunoassays.

Biomarker expression may also be by PCR methods, including for example, real time PCR. See for example, U.S. Pat. Nos. 5,723,591; 5,801,155 and 6,084,102 and Higuchi, 1992 and 1993. PCR assays may be done, for example, in a multi-well plate formats or in chips, such as the BioTrove OpenArray™ Chips (BioTrove, Woburn, Mass.).

If desired, the sample can be prepared to enhance detectability of the markers. For example, to increase the detectability of protein markers, a blood serum sample from the subject can be preferably fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In one embodiment, a sample can be pre-fractionated according to size of proteins in a sample using size exclusion chromatography. For a biological sample wherein the amount of sample available is small, preferably a size selection spin column is used. For example, a K30 spin column (available from Princeton Separation, Ciphergen Biosystems, Inc., etc.) can be used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by gas phase ion spectrometry for the detection of markers.

In another embodiment, a sample can be pre-fractionated by anion exchange chromatography. Anion exchange chromatography allows pre-fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be pre-fractionated by heparin chromatography. Heparin chromatography allows pre-fractionation of the markers in a sample also on the basis of affinity interaction with heparin and charge characteristics. Heparin, a sulfated mucopolysaccharide, will bind markers with positively charged moieties and a sample can be sequentially eluted with eluants having different pH's or salt concentrations. Markers eluted with an eluant having a low pH are more likely to be weakly positively charged. Markers eluted with an eluant having a high pH are more likely to be strongly positively charged. Thus, heparin chromatography also reduces the complexity of a sample and separates markers according to their binding characteristics.

In yet another embodiment, a sample can be pre-fractionated by removing proteins that are present in a high quantity or that may interfere with the detection of markers in a sample. For example, in a blood serum sample, serum albumin is present in a high quantity and may obscure the analysis of markers. Thus, a blood serum sample can be pre-fractionated by removing serum albumin. Serum albumin can be removed using a substrate that comprises adsorbents that specifically bind serum albumin. For example, a column which comprises, e.g., Cibacron blue agarose (which has a high affinity for serum albumin) or anti-serum albumin antibodies can be used.

In yet another embodiment, a sample can be pre-fractionated by isolating proteins that have a specific characteristic, e.g. are glycosylated. For example, a blood serum sample can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

Many types of affinity adsorbents exist which are suitable for pre-fractionating blood serum samples. An example of one other type of affinity chromatography available to pre-fractionate a sample is a single stranded DNA spin column. These columns bind proteins which are basic or positively charged. Bound proteins are then eluted from the column using eluants containing denaturants or high pH.

Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomolecules from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomolecules. In this embodiment, the sample is applied to a first adsorbent on the probe, which is subsequently washed with an eluant. Markers that do not bind to the first adsorbent is removed with an eluant. The markers that are in the fraction can be applied to a second adsorbent on the probe, and so forth. The advantage of performing sequential extraction on a gas phase ion spectrometer probe is that markers that bind to various adsorbents at every stage of the sequential extraction protocol can be analyzed directly using a gas phase ion spectrometer.

In yet another embodiment, biomolecules in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomolecules, including one or more markers. See, e.g., Jungblut and Thiede, *Mass Spectr. Rev.* 16:145-162 (1997).

The two-dimensional gel electrophoresis can be performed using methods known in the art. See, e.g., Deutscher ed., *Methods In Enzymology* vol. 182. Typically, biomolecules in a sample are separated by, e.g., isoelectric focusing, during which biomolecules in a sample are separated in a pH gradient until they reach a spot where their net charge is zero (i.e., isoelectric point). This first separation step results in one-dimensional array of biomolecules. The biomolecules in one-dimensional array is further separated using a technique generally distinct from that used in the first separation step. For example, in the second dimension, biomolecules separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomolecules. Typically, two-dimensional gel electrophoresis can separate chemically different biomolecules in the molecular mass range from 1000-200,000 Da within complex mixtures.

Biomolecules in the two-dimensional array can be detected using any suitable methods known in the art. For example, biomolecules in a gel can be labeled or stained (e.g., Coomassie Blue or silver staining). If gel electrophoresis generates spots that correspond to the molecular weight of one or more markers of the invention, the spot can be is further analyzed by gas phase ion spectrometry. For example, spots can be excised from the gel and analyzed by gas phase ion spectrometry. Alternatively, the gel containing biomolecules can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using ProteinChip® array) as described in detail below.

Prior to gas phase ion spectrometry analysis, it may be desirable to cleave biomolecules in the spot into smaller fragments using cleaving reagents, such as proteases (e.g., trypsin). The digestion of biomolecules into small fragments provides a mass fingerprint of the biomolecules in the spot, which can be used to determine the identity of markers if desired.

In yet another embodiment, high performance liquid chromatography (HPLC) can-be used to separate a mixture of biomolecules in a sample based on their different physical properties, such as polarity, charge and size. HPLC instruments typically consist of a reservoir of mobile phase, a pump, an injector, a separation column, and a detector. Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers. For example, the spots can be analyzed using either MALDI or SELDI (e.g., using ProteinChip® array) as described in detail below.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In another example, biomolecules can be modified to improve detection resolution. For instance, neuraminidase can be used to remove terminal sialic acid residues from glycoproteins to improve binding to an anionic adsorbent (e.g., cationic exchange ProteinChip® arrays) and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt).

Detection and Measurement of Markers

Once captured on a substrate, e.g., biochip or antibody, any suitable method can be used to measure a marker or markers in a sample. For example, markers can be detected and/or measured by a variety of detection methods including for example, gas phase ion spectrometry methods, optical methods, electrochemical methods, atomic force microscopy, radio frequency methods, surface plasmon resonance, ellipsometry and atomic force microscopy.

SELDI

One preferred method of detection and/or measurement of the biomarkers uses mass spectrometry, and in particular, "Surface-enhanced laser desorption/ionization" or "SELDI". SELDI refers to a method of desorption/ionization gas phase ion spectrometry (e.g., mass spectrometry) in which the analyte is captured on the surface of a SELDI probe that engages the probe interface. In "SELDI MS," the gas phase ion spectrometer is a mass spectrometer. SELDI technology is described in more detail above and as follows.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of markers or other substances will typically involve detection of signal intensity. This, in turn, can reflect the quantity and character of markers bound to the substrate. Any of the components of a mass spectrometer (e.g., a desorption source, a mass analyzer, a detector, etc.) can be combined with other suitable components described herein or others known in the art in embodiments of the invention.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

In another embodiment, an ion mobility spectrometer can be used to detect markers. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in a sample. One advantage of ion mobility spectrometry is that it can operate at atmospheric pressure.

In yet another embodiment, a total ion current measuring device can be used to detect and characterize markers. This device can be used when the substrate has a only a single type of marker. When a single type of marker is on the substrate, the total current generated from the ionized marker reflects the quantity and other characteristics of the marker. The total ion current produced by the marker can then be compared to a control (e.g., a total ion current of a known compound). The quantity or other characteristics of the marker can then be determined.

Immunoassay

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

An immunoassay is an assay that uses an antibody to specifically bind an antigen (e.g., a marker). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a marker from specific species such as rat, mouse, or human can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

Using the purified markers or their nucleic acid sequences, antibodies that specifically bind to a marker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)). Typically a specific or selective reaction will be at least twice background signal or noise and more typically more than 10 to 100 times background.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological fluid sample taken from a subject. Examples of biological fluid samples include blood, serum, plasma, nipple aspirate, urine, tears, saliva etc. In a preferred embodiment, the biological fluid comprises blood serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology. Antibodies in Cell Biology*, volume 37 (Asai, ed. 1993); *Basic and Clinical Immunology* (Stites & Terr, eds., 7th ed. 1991); and Harlow & Lane, supra.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid melanoma diagnosis or prognosis. In another example, the methods for detection of the markers can be used to monitor responses in a subject to melanoma treatment. In another example, the methods for detecting markers can be used to assay for and to identify compounds that modulate expression of these markers in vivo or in vitro. In a preferred example, the biomarkers are used to differentiate between the different stages of tumor progression, thus aiding in determining appropriate treatment and extent of metastasis of the tumor.

Use of Modified Forms of a Biomarker

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. The collection of proteins including a specific protein and all modified forms of it is referred to herein as a "protein cluster." The collection of all modified forms of a specific protein, excluding the specific protein, itself, is referred to herein as a "modified protein cluster." Modified forms of any biomarker of this invention (including any of Markers 1-104) also may be used, themselves, as biomarkers. In certain cases the modified forms may exhibit better discriminatory power in diagnosis than the specific forms set forth herein.

Modified forms of a biomarker including any of Markers 1-104 can be initially detected by any methodology that can detect and distinguish the modified from the biomarker. A preferred method for initial detection involves first capturing the biomarker and modified forms of it, e.g., with biospecific capture reagents, and then detecting the captured proteins by mass spectrometry. More specifically, the proteins are captured using biospecific capture reagents, such as antibodies, aptamers or Affibodies that recognize the biomarker and modified forms of it. This method also will also result in the capture of protein interactors that are bound to the proteins or that are otherwise recognized by antibodies and that, themselves, can be biomarkers. Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

Preferably, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody-derivatized bead-based technologies, such as xMAP technology of Luminex (Austin, Tex.) can be used to detect the protein clusters. However, the biospecific capture reagents must be specifically directed toward the members of a cluster in order to differentiate them.

In yet another embodiment, the surfaces of biochips can be derivatized with the capture reagents directed against protein clusters either in the same location or in physically different addressable locations. One advantage of capturing different clusters in different addressable locations is that the analysis becomes simpler.

After identification of modified forms of a protein and correlation with the clinical parameter of interest, the modified form can be used as a biomarker in any of the methods of this invention. At this point, detection of the modified from can be accomplished by any specific detection methodology including affinity capture followed by mass spectrometry, or traditional immunoassay directed specifically the modified form. Immunoassay requires biospecific capture reagents, such as antibodies, to capture the analytes. Furthermore, if the assay must be designed to specifically distinguish protein and modified forms of protein. This can be done, for example, by employing a sandwich assay in which one antibody captures more than one form and second, distinctly labeled antibodies, specifically bind, and provide distinct detection of, the various forms. Antibodies can be produced by immunizing animals with the biomolecules. This invention contemplates traditional immunoassays including, for example, sandwich immunoassays including ELISA or fluorescence-based immunoassays, as well as other enzyme immunoassays.

Data Analysis

The methods for detecting these markers in a sample have many applications. For example, one or more markers can be measured to aid human melanoma diagnosis or prognosis. In another example, the methods for detection of the markers can be used to monitor responses in a subject to melanoma treatment. In another example, the methods for detecting markers can be used to assay for and to identify compounds that modulate expression of these markers in vivo or in vitro.

Differentiation of non-melanoma and melanoma status may be by the detection of one or more of the Markers listed in Tables 1-3 or the Markers described as proteins or pathways for melanoma. For example, an exemplary marker that may independently discriminate between colorectal and non-colorectal status is Markers 1-104. Combinations of markers are also useful in the methods of the invention for the determination melanoma and melanoma status. Markers may be detected, determined, monitored in a sample by molecular biological methods, including, immunological, arrays (nucleic acid, protein), PCR methods (real-time, reverse transcriptase, PCR).

Detection of markers can be analyzed using any suitable means, including arrays. Nucleic acid arrays may be analyzed using software, for example, Applied Maths, Belgium. GenExplore™: 2-way cluster analysis, principal component analysis, discriminant analysis, self-organizing maps; BioDiscovery, Inc., Los Angeles, Calif. (ImaGene™, special image processing and data extraction software, powered by MatLab®; GeneSight: hierarchical clustering, artificial neural network (SOM?), principal component analysis, time series; AutoGene™; CloneTracker™); GeneData AG (Basel, Switzerland); Molecular Pattern Recognition web site at MIT's Whitehead Genome Center; Rosetta Inpharmatics, Kirkland, Wash. Resolver™ Expression Data Analysis System; Scanalytics, Inc., Fairfax, Va. Its MicroArray Suite enables researchers to acquire, visualize, process, and analyze gene expression microarray data; TIGR (The Institute for Genome Research) offers software tools (free for academic institutions) for array analysis. For example, see also Eisen M B, Brown P O., Methods Enzymol. 1999; 303:179-205.

Detection of markers can be analyzed using any suitable means. In one embodiment, the four-step data reduction algorithm developed by B. Ryu is utilized (Ryu B, Jones J, Blades N J, Parmigiani G, Hollingsworth M A and Hruban R. Relationships and Differentially Expressed Genes among Pancreatic Cancers examined by Large-scale Serial Analysis of Gene Expression. Cancer Res 2002; 62:819-826). For example, group comparison was performed using Student's t test. Next, fold differences were evaluated and only those genes with a five-fold or greater expression were kept. The third step involves filtration by sample criteria. However, this step was not applied in this circumstance as expression profiling data from primary melanoma tissue samples was not yet available. In the final step, the genes were further reduced according to the degree of up-regulated expression (Norgauer J, Metzner B, Schraufstatter I. Expression and growth-promoting function of the IL-8 receptor beta in human melanoma cells. J. Immunol. 1996; 156(3):1132-1137).

In one embodiment, data generated, for example, by desorption is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a serum protein) may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., men in whom human melanoma is undetectable).

When the sample is measured and data is generated, e.g., by mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and melanoma and determines the closeness of fit between the two signals. The software also can include code indicating which the test sample is closest to, thereby providing a probable diagnosis.

In preferred methods of the present invention, multiple biomarkers are measured. The use of multiple biomarkers increases the predictive value of the test and provides greater utility in diagnosis, toxicology, subject stratification and subject monitoring. The process called "Pattern recognition" detects the patterns formed by multiple biomarkers greatly improves the sensitivity and specificity of clinical proteomics for predictive medicine. Subtle variations in data from clinical samples, e.g., obtained using SELDI, indicate that certain patterns of protein expression can predict phenotypes such as the presence or absence of a certain disease, a particular stage of melanoma-progression, or a positive or adverse response to drug treatments.

Data generation in mass spectrometry begins with the detection of ions by an ion detector as described above. Ions that strike the detector generate an electric potential that is digitized by a high speed time-array recording device that digitally captures the analog signal. Ciphergen's Protein-Chip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering.

TOF-to-M/Z transformation involves the application of an algorithm that transforms times-of-flight into mass-to-charge ratio (M/Z). In this step, the signals are converted from the time domain to the mass domain. That is, each time-of-flight is converted into mass-to-charge ratio, or M/Z. Calibration can be done internally or externally. In internal calibration, the sample analyzed contains one or more analytes of known M/Z. Signal peaks at times-of-flight representing these massed analytes are assigned the known M/Z. Based on these assigned M/Z ratios, parameters are calculated for a mathematical function that converts times-of-flight to M/Z. In external calibration, a function that converts times-of-flight to M/Z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

Analysis generally involves the identification of peaks in the spectrum that represent signal from an analyte. Peak selection can, of course, be done by eye. However, software is available as part of Ciphergen's ProteinChip® software that can automate the detection of peaks. In general, this software functions by identifying signals having a signal-to-noise ratio above a selected threshold and labeling the mass of the peak at the centroid of the peak signal. In one useful application many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

The spectra that are generated in embodiments of the invention can be classified using a pattern recognition process that uses a classification model. In some embodiments, data derived from the spectra (e.g., mass spectra or time-of-flight spectra) that are generated using samples such as "known samples" can then be used to "train" a classification model. A "known sample" is a sample that is pre-classified (e.g., melanoma or not melanoma). Data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The training data set that is used to form the classification model may comprise raw data or pre-processed data. In some embodiments, raw data can be obtained directly from time-of-flight spectra or mass spectra, and then may be optionally "pre-processed" in any suitable manner. For example, signals above a predetermined signal-to-noise ratio can be selected so that a subset of peaks in a spectrum is selected, rather than selecting all peaks in a spectrum. In another example, a pre-determined number of peak "clusters" at a common value (e.g., a particular time-of-flight value or mass-to-charge ratio value) can be used to select peaks. Illustratively, if a peak at a given mass-to-charge ratio is in less than 50% of the mass spectra in a group of mass spectra, then the peak at that mass-to-charge ratio can be omitted from the training data set. Pre-processing steps such as these can be used to reduce the amount of data that is used to train the classification model.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. 2002 0138208 A1 (Paulse et al., "Method for analyzing mass spectra," Sep. 26, 2002).

In other embodiments, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described in, for example, WO 01/31580 (Barnhill et al., "Methods and devices for identifying patterns in biological systems and methods of use thereof," May 3, 2001); U.S. 2002/0193950 A1 (Gavin et al., "Method or analyzing mass spectra," Dec. 19, 2002); U.S. 2003/0004402 A1 (Hitt et al., "Process for discriminating between biological states based on hidden patterns from biological data," Jan. 2, 2003); and U.S. 2003/0055615 A1 (Zhang and Zhang, "Systems and methods for processing biological expression data" Mar. 20, 2003).

More specifically, to obtain the biomarkers the peak intensity data of samples from subjects, e.g., melanoma subjects, and healthy controls are used as a "discovery set." This data were combined and randomly divided into a training set and a test set to construct and test multivariate predictive models using a non-linear version of Unified Maximum Separability Analysis ("USMA") classifiers. Details of USMA classifiers are described in U.S. 2003/0055615 A1.

The invention provides methods for aiding a human melanoma diagnosis using one or more markers, for example Markers in the tables and figures which follow, and including one or more Markers 1-104 as specified herein. These markers can be used alone, in combination with other markers in any set, or with entirely different markers in aiding human melanoma diagnosis. The markers are differentially present in samples of a human melanoma subject and a normal subject in whom human melanoma is undetectable. For example, some of the markers are expressed at an elevated level and/or are present at a higher frequency in human melanoma subjects than in normal subjects, while some of the markers are expressed at a decreased level and/or are present at a lower frequency in human melanoma subjects than in normal subjects. Therefore, detection of one or more of these markers in a person would provide useful information regarding the probability that the person may have melanoma.

Differentiation Between Normal and Unaffected Disease Tissue

The invention provides methods for aiding a human melanoma diagnosis using one or more markers, for example Markers in the tables and figures herein, and including one or more Markers 1-104 as specified herein. These markers can be used alone, in combination with other markers in any set, or with entirely different markers in aiding human melanoma diagnosis. The markers are differentially present in samples of a human melanoma subject and a normal subject in whom human melanoma is undetectable. For example, some of the markers are expressed at an elevated level and/or are present at a higher frequency in human melanoma subjects than in normal subjects, while some of the markers are expressed at a decreased level and/or are present at a lower frequency in human melanoma subjects than in normal subjects. Therefore, detection of one or more of these markers in a person would provide useful information regarding the probability that the person may have melanoma.

In a preferred embodiment, a biological sample is collected from a subject and then either left unfractionated, or fractionated using an anion exchange resin as described above. The biomarkers in the sample are captured using an ProteinChip array. The markers are then detected using SELDI. The results are then entered into a computer system, which contains an algorithm that is designed using the same parameters that were used in the learning algorithm and classification algorithm to originally determine the biomarkers. The algorithm produces a diagnosis based upon the data received relating to each biomarker.

The diagnosis is determined by examining the data produced from the tests with algorithms that are developed using the biomarkers. The algorithms depend on the particulars of the test protocol used to detect the biomarkers. These particulars include, for example, sample preparation, chip type and mass spectrometer parameters. If the test parameters change, the algorithm must change. Similarly, if the algorithm changes, the test protocol must change.

In another embodiment, the sample is collected from the subject. The biomarkers are captured using an antibody ProteinChip array as described above. The markers are detected using a biospecific SELDI test system. The results are then entered into a computer system, which contains an algorithm that is designed using the same parameters that were used in the learning algorithm and classification algorithm to originally determine the biomarkers. The algorithm produces a diagnosis based upon the data received relating to each biomarker.

In yet other preferred embodiments, the markers are captured and tested using non-SELDI formats. In one example, the sample is collected from the subject. The biomarkers are captured on a substrate using other known means, e.g., antibodies to the markers. The markers are detected using methods known in the art, e.g., optical methods and refractive index. Examples of optical methods include detection of fluorescence, e.g., ELISA. Examples of refractive index include surface plasmon resonance. The results for the markers are then subjected to an algorithm, which may or may not require artificial intelligence. The algorithm produces a diagnosis based upon the data received relating to each biomarker.

In any of the above methods, the data from the sample may be fed directly from the detection means into a computer containing the diagnostic algorithm. Alternatively, the data obtained can be fed manually, or via an automated means, into a separate computer that contains the diagnostic algorithm.

Accordingly, embodiments of the invention include methods for aiding a human melanoma diagnosis, wherein the method comprises: (a) detecting at least one marker in a sample, wherein the marker is selected from any of the Markers 1-104; and (b) correlating the detection of the marker or markers with a probable diagnosis of human melanoma. The correlation may take into account the amount of the marker or markers in the sample compared to a control amount of the marker or markers (up or down regulation of the marker or markers) (e.g., in normal subjects in whom human melanoma is undetectable). The correlation may take into account the presence or absence of the markers in a test sample and the frequency of detection of the same markers in a control. The correlation may take into account both of such factors to facilitate determination of whether a subject has a human melanoma or not.

In a preferred embodiment, Markers 1-104 are used to make a correlation with melanoma, wherein the melanoma may be any subtype, e.g., superficial spreading, nodular, acrolentiginous, and lentigo maligna.

Any suitable samples can be obtained from a subject to detect markers. Preferably, a sample is a blood sample or a tissue biopsy. If desired, the sample can be prepared as described above to enhance detectability of the markers. For example, to increase the detectability of markers, a sample from the subject can be preferably fractionated by, e.g., Cibacron blue agarose chromatography and single stranded DNA affinity chromatography, anion exchange chromatography and the like. Sample preparations, such as pre-fractionation protocols, are optional and may not be necessary to enhance detectability of markers depending on the methods of detection used. For example, sample preparation may be unnecessary if antibodies that specifically bind markers are used to detect the presence of markers in a sample.

Processes for the purification of a biomarker include fractioning a sample, as described herein, for example, by size-exclusion chromatography and collecting a fraction that includes one or more biomarkers; and/or fractionating a sample comprising the one or more biomarkers by anion exchange chromatography and collecting a fraction that includes one or more biomarkers, wherein the biomarker is selected from one or more of the biomarkers of Tables 1-3.

Diagnosis of Subject and Determination of Melanoma Status

Any biomarker, individually, is useful in aiding in the determination of melanoma status. First, the selected biomarker is measured in a subject sample using the methods described herein, e.g., capture on a SELDI biochip followed by detection by mass spectrometry or by immunoassay or microarray. Then, the measurement is compared with a diagnostic amount or control that distinguishes a melanoma status from a non-melanoma status. The diagnostic amount will reflect the information herein that a particular biomarker is up-regulated or down-regulated in a melanoma status compared with a non-melanoma status. As is well understood in the art, the particular diagnostic amount used can be adjusted to increase sensitivity or specificity of the diagnostic assay depending on the preference of the diagnostician. The test amount as compared with the diagnostic amount thus indicates melanoma status.

While individual biomarkers are useful diagnostic markers, combination of biomarkers provide predictive value as well. Specifically, the detection of a plurality of markers in a sample increases the percentage of true positive and true negative diagnoses and would decrease the percentage of false positive or false negative diagnoses. Thus, methods of the present invention comprise the measurement of more than one biomarker.

The detection of the marker or markers is then correlated with a probable diagnosis of melanoma. In some embodiments, the detection of the mere presence or absence of a marker, without quantifying the amount of marker, is useful and can be correlated with a probable diagnosis of melanoma. For example, biomarkers 1-104 can be more frequently detected in human melanoma subjects than in normal subjects. A mere detection of one or more of these markers in a subject being tested indicates that the subject has a higher probability of having melanoma.

In other embodiments, the measurement of markers can involve quantifying the markers to correlate the detection of markers with a probable diagnosis of melanoma. Thus, if the amount of the markers detected in a subject being tested is different compared to a control amount (i.e., higher or lower than the control, depending on the marker), then the subject being tested has a higher probability of having melanoma.

The correlation may take into account the amount of the marker or markers in the sample compared to a control amount of the marker or markers (up or down regulation of the marker or markers) (e.g., in normal subjects or in non-melanoma subjects such as where melanoma is undetectable). A control can be, e.g., the average or median amount of marker present in comparable samples of normal subjects in normal subjects or in non-melanoma subjects such as where melanoma is undetectable. The control amount is measured under the same or substantially similar experimental conditions as in measuring the test amount. The correlation may take into account the presence or absence of the markers in a test sample and the frequency of detection of the same markers in a control. The correlation may take into account both of such factors to facilitate determination of melanoma status.

In certain embodiments of the methods of qualifying melanoma status, the methods further comprise managing subject treatment based on the status. As before the management of the subject describes the actions of the physician or clinician subsequent to determining melanoma status. For example, if the result of the methods of the present invention is inconclusive or there is reason that confirmation of status is necessary, the physician may order more tests (e.g., CT_scans, PET scans, MRI scans, PET-CT scans, X-rays, biopsies, blood tests (LFTs, LDH)_). Alternatively, if the status indicates that treatment is appropriate, the physician may schedule the subject for treatment. In other instances, the subject may receive therapeutic treatments, either in lieu of, or in addition to, surgery. No further action may be warranted. Furthermore, if the results show that treatment has been successful, a maintenance therapy or no further management may be necessary.

Therapeutic agents may include, one or more of fotemustine, dacarbazine, interferon, cisplatin, tamoxifen, interleukin-2, ifn alfa, vinblastin, or orcarmubris.

The invention also provides for such methods where the biomarkers (or specific combination of biomarkers) are measured again after subject management. In these cases, the methods are used to monitor the status of the melanoma, e.g., response to melanoma treatment, remission of the disease or progression of the disease. Because of the ease of use of the methods and the lack of invasiveness of the methods, the methods can be repeated after each treatment the subject receives. This allows the physician to follow the effectiveness of the course of treatment. If the results show that the treatment is not effective, the course of treatment can be altered accordingly. This enables the physician to be flexible in the treatment options.

In another example, the methods for detecting markers can be used to assay for and to identify compounds that modulate expression of these markers in vivo or in vitro.

The methods of the present invention have other applications as well. For example, the markers can be used to screen for compounds that modulate the expression of the markers in vitro or in vivo, which compounds in turn may be useful in treating or preventing melanoma in subjects. In another example, the markers can be used to monitor the response to treatments for melanoma. In yet another example, the markers can be used in heredity studies to determine if the subject is at risk for developing melanoma. For instance, certain markers may be genetically linked. This can be determined by, e.g., analyzing samples from a population of melanoma subjects whose families have a history of melanoma. The results can then be compared with data obtained from, e.g., melanoma subjects whose families do not have a history of melanoma. The markers that are genetically linked may be used as a tool to determine if a subject whose family has a history of melanoma is pre-disposed to having melanoma.

In a preferred embodiment of the invention, a diagnosis based on the presence or absence in a test subject of any the biomarkers of this invention is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

Methods of the invention for determining the melanoma status of a subject, include for example, obtaining a biomarker profile from a sample taken from the subject; and comparing the subject's biomarker profile to a reference biomarker profile obtained from a reference population, wherein the comparison is capable of classifying the subject as belonging to or not belonging to the reference population; wherein the subject's biomarker profile and the reference biomarker profile comprise one or more markers listed in Tables 1-3.

The method may further comprise repeating the method at least once, wherein the subject's biomarker profile is obtained from a separate sample taken each time the method is repeated.

Samples from the subject may be taken at any time, for example, the samples may be taken 24 hours apart or any other time determined useful.

Such comparisons of the biomarker profiles can determine melanoma status in the subject with an accuracy of at least about 60%, 70%, 80%, 90%, 95%, and approaching 100% as shown in the examples which follow.

The reference biomarker profile can be obtained from a population comprising a single subject, at least two subjects, at least 20 subjects or more. The number of subjects will depend, in part, on the number of available subjects, and the power of the statistical analysis necessary.

A method of treating melanoma comprising administering to a subject suffering from or at risk of developing melanoma a therapeutically effective amount of a compound capable of modulating the expression or activity of one or more of the biomarkers of Tables 1-3.

A method of treating a condition in a subject comprising administering to a subject a therapeutically effective amount of a compound which modulates the expression or activity of one or more of the biomarkers of Tables 1-3.

Compounds useful in methods disclosed herein include, for example, fotemustine, dacarbazine, interferon, cisplatin, tamoxifen, interleukin-2, ifr alfa, vinblastin, or orcarmubris.

A method of qualifying melanoma status in a subject comprising:

(a) measuring at least one biomarker in a sample from the subject, wherein the biomarker is selected from one or more of the biomarkers of Tables 1-3, and (b) correlating the measurement with melanoma status.

The method may also comprise the step of measuring the at least one biomarker after subject management.

Optionally, the methods of the invention may further comprise generating data on immobilized subject samples on a biochip, by subjecting the biochip to laser ionization and detecting intensity of signal for mass/charge ratio; and transforming the data into computer readable form; and executing an algorithm that classifies the data according to user input parameters, for detecting signals that represent biomarkers present in melanoma subjects and are lacking in non-melanoma subject controls.

Types or stages of melanoma that may be identified or differentiated from one another according to this method include, stages 0, I-IV and recurrent melanoma.

Kits

In one aspect, the invention provides kits for the analysis of melanoma status. The kits include PCR primers for at least one marker selected from Markers 1-37. In preferred embodiments, the kit includes more than two or three markers selected from Markers 1-37. The kit may further include instructions for use and correlation of the maker with disease status. The kit may also include a DNA array containing the complement of one or more of the Markers selected from 1-37, reagents, and/or enzymes for amplifying or isolating sample DNA. The kits may include reagents for real-time PCR, for example, TaqMan probes and/or primers, and enzymes.

In yet another aspect, the invention provides kits for qualifying melanoma status and/or aiding a diagnosis of human melanoma, wherein the kits can be used to detect the markers of the present invention. For example, the kits can be used to detect any one or more of the markers described herein, which markers are differentially present in samples of melanoma subjects and normal subjects. The kits of the invention have many applications. For example, the kits can be used to differentiate if a subject has melanoma or has a negative diagnosis, thus aiding a human melanoma diagnosis. In another example, the kits can be used to identify compounds that modulate expression of one or more of the markers in in vitro or in vivo animal models for melanoma.

In one embodiment, a kit comprises: (a) a substrate comprising an adsorbent thereon, wherein the adsorbent is suitable for binding a marker, and (b) instructions to detect the marker or markers by contacting a sample with the adsorbent and detecting the marker or markers retained by the adsorbent. In some embodiments, the kit may comprise an eluant (as an alternative or in combination with instructions) or instructions for making an eluant, wherein the combination of the adsorbent and the eluant allows detection of the markers using gas phase ion spectrometry.

Such kits can be prepared from the materials described above, and the previous discussion of these materials (e.g., probe substrates, adsorbents, washing solutions, etc.) is fully applicable to this section and will not be repeated.

In another embodiment, the kit may comprise a first substrate comprising an adsorbent thereon (e.g., a particle functionalized with an adsorbent) and a second substrate onto which the first substrate can be positioned to form a probe, which is removably insertable into a gas phase ion spectrometer. In other embodiments, the kit may comprise a single substrate, which is in the form of a removably insertable probe with adsorbents on the substrate. In yet another embodiment, the kit may further comprise a pre-fractionation spin column (e.g., Cibacron blue agarose column, anti-HSA agarose column, K-30 size exclusion column, Q-anion exchange spin column, single stranded DNA column, lectin column, etc.).

In another embodiment, a kit comprises (a) an antibody that specifically binds to a marker; and (b) a detection reagent. Such kits can be prepared from the materials described above, and the previous discussion regarding the materials (e.g., antibodies, detection reagents, immobilized supports, etc.) is fully applicable to this section and will not be repeated.

Optionally, the kit may further comprise pre-fractionation spin columns. In some embodiments, the kit may further comprise instructions for suitable operation parameters in the form of a label or a separate insert.

Optionally, the kit may further comprise a standard or control information so that the test sample can be compared with the control information standard to determine if the test amount of a marker detected in a sample is a diagnostic amount consistent with a diagnosis of melanoma.

Melanoma Candidate Genes and Use of Biomarkers for Melanoma in Screening Assays

In one aspect the invention also includes melanoma candidate genes, which are useful as therapeutic targets. These genes include, for example, those listed in Tables 1-3. Other candidate genes may be identified by, for example, the methods described herein. Useful methods to identify melanoma candidate genes useful as candidate drug targets include those used to identify the candidate therapeutic targets listed in Tables 1-3.

Candidate genes useful as therapeutic agents include those that are up- and down-regulated in melanoma compared to controls or reference samples. Candidate genes may also be useful as therapeutic agents, for example, for gene replacement therapy of down-regulated genes and proteins.

The methods of the present invention have other applications as well. For example, the biomarkers can be used to screen for compounds that modulate the expression of the biomarkers in vitro or in vivo, which compounds in turn may be useful in treating or preventing melanoma in subjects. In another example, the biomarkers can be used to monitor the response to treatments for melanoma. In yet another example, the biomarkers can be used in heredity studies to determine if the subject is at risk for developing melanoma.

Thus, for example, the kits of this invention could include a solid substrate having a hydrophobic function, such as a protein biochip (e.g., a Ciphergen ProteinChip array) and a buffer for washing the substrate, as well as instructions providing a protocol to measure the biomarkers of this invention on the chip and to use these measurements to diagnose melanoma.

Method for identifying a candidate compound for treating melanoma may comprise, for example, contacting one or more of the biomarkers of Tables 1-3 with a test compound; and determining whether the test compound interacts with the biomarker, wherein a compound that interacts with the biomarker is identified as a candidate compound for treating melanoma.

Compounds suitable for therapeutic testing may be screened initially by identifying compounds which interact with one or more biomarkers listed in identified herein. By way of example, screening might include recombinantly expressing a biomarker of this invention, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of this invention, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of this invention may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of this invention may also be measured. For example, the self-assembly of a multi-protein complex which includes one of the biomarkers of this invention may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of this invention may be administered to subjects who are suffering from or are at risk of developing melanoma. For example, the administration of a test compound which increases the activity of a particular biomarker may decrease the risk of melanoma in a subject if the activity of the particular biomarker in vivo prevents the accumulation of proteins for melanoma. Conversely, the administration of a test compound which decreases the activity of a particular biomarker may decrease the risk of melanoma in a subject if the increased activity of the biomarker is responsible, at least in part, for the onset of melanoma.

At the clinical level, screening a test compound includes obtaining samples from test subjects before and after the subjects have been exposed to a test compound. The levels in the samples of one or more of the biomarkers of this invention may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers of this invention may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which-express, or are capable of expressing, one or more of the biomarkers of this invention may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with melanoma, test compounds will be screened for their ability to slow or stop the progression of the disease.

Methods of identifying therapeutic targets for melanoma generally comprise comparing an expression profile of a melanoma cell with an expression profile of one a reference cell, wherein the comparison is capable of classifying proteins or transcripts in the profile as being associated with melanoma invasion.

Reference cells may be normal cells (cells that are not melanoma cells) or melanoma cells a different stage from the melanoma cells being compared to. The reference cells may be primary cultured cells, fresh blood cells, established cell lines or other cells determined to be appropriate to one of skill in the art. Transcripts and proteins associated with melanoma invasion include cells that differentiate between the states of melanoma and between normal and melanoma cell lines. The transcripts and proteins may also differentiate between melanoma and other forms of cancer. The proteins may be secreted proteins, such that they are easily detectable from a blood sample.

Classification Algorithms

A dataset can be analyzed by multiple classification algorithms. Some classification algorithms provide discrete rules for classification; others provide probability estimates of a certain outcome (class). In the latter case, the decision (diagnosis) is made based on the class with the highest probability. For example, consider the three-class problem: healthy, benign, and melanoma. Suppose that a classification algorithm (e.g. Nearest neighbor) is constructed and applied to sample A, and the probability of the sample being healthy is 0, benign is 33%, and melanoma is 67%. Sample A would be diagnosed as being melanoma. This approach, however, does not take into account any "fuzziness" in the diagnosis, e.g., that there was a certain probability that the sample was benign. Therefore, the diagnosis would be the same as for sample B, which has a probability of 0 of being healthy or benign and a probability of 1 of being melanoma.

EXAMPLES

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

It should be appreciated that the invention should not be construed to be limited to the examples which are now described; rather, the invention should be construed to include any and all applications provided herein and all equivalent variations within the skill of the ordinary artisan.

Example 1

Identification of Novel Melanoma Markers using Gene Expression Profiling

Tumor markers were identified due to overexpression of their mRNA in affected cells and many tumor markers in clinical use today were originally identified in such a manner. It is assumed that melanoma, like other tumors, evolves due to a sequence of genetic and epigenetic events that occur over time. While the genetic events that occur in the evolution of other tumors like colon and breast cancers have been thoroughly investigated, systematic evaluation of melanoma for such genetic or epigenetic changes has lagged behind. This is due, in large part, to the lack of available tissue for investigation of progressive melanocytic lesions and a relative uncertainty regarding the true precursor lesions in melanoma. A series of melanoma cell lines were prepared from primary human tumors of varying degrees of malignant progression. These lines have shown a remarkable recapitulation of expression patterns seen in primary human tissue and were used to initially assess gene expression profiles from melanomas at different stages of malignant progression. Genes identified as being differentially expressed in a stage-specific fashion are further analyzed using clinical outcomes data to determine markers that may be of prognostic utility. Markers deemed to be of greatest clinical relevance are further analyzed in in-vivo assessments.

Assessment of Gene Expression Profiles of Melanoma Cell Lines from Varying Stages of Malignant Progression A major problem with evaluating expression profiles from melanocytic lesions and melanomas has been the lack of primary tissue specimens from which intact RNA can be readily extracted. Although recent work using expression profiling has allowed for subclassification of melanomas based on global transcript patterns[3], these data were of limited utility since the primary specimens were from advanced stages of disease and mRNAs used for analysis were not obtained from microdissected specimens thus analysis included transcript from non-melanocytic cells which may have skewed the data obtained. Others have evaluated metastatic melanoma cell lines by gene expression profiling[4] and have been able to confirm the significance of particular genetic alterations in late-stage melanomas using this method. Since standard analysis of melanomas and other melanocytic lesions involves hematoxylin and eosin (H&E) staining of formalin-fixed, paraffin-embedded tissues, the availability of early primary melanocytic lesions for microarray analysis is limited.

Ten (10) melanoma cell lines derived from varying stages of malignant progression[5] were obtained and initial studies to assess the expression of genes of interest were performed. Since it was found that expression of the HLH protein Id1 was upregulated in radial growth phase melanomas using in-situ hybridization on primary melanomas[6], there was interested in assessing whether this expression pattern would be recapitulated in the cell lines obtained. Id1 was found to be expressed in all three radial growth phase cell lines obtained by both transcript and protein analysis and to be undetectable in any of the later stage melanomas or primary human melanocytes. This data suggested that the cell lines could be used to screen for genes of interest that are aberrantly expressed during the process of melanoma development and progression. Without wishing to be bound by theory, since the progression from radial growth phase (RGP) to vertical growth phase (VGP) is important for the development of metastatic disease, identification of markers to delineate the growth phase of a particular melanocytic lesion will be critical for determining prognosis and treatment strategies.

The expression profiles of 10 melanoma cell lines from various stages of malignant progression were evaluated (3 radial-growth phase (RGP), 1 early vertical-growth phase (VGP), 3 late VGP, 3 metastatic melanomas) as well as pools of primary human melanocytes derived from neonatal foreskins, using the Affimetrix Human Genome U133 Set. This set consists of 2 gene chip arrays which contain nearly 45,000 probe sets that represent more than 39,000 transcripts including 33,000 well-substantiated human genes and over 10,000 ESTs. mRNAs were prepared from all cell lines using the TRIzol protocol for RNA isolation. Total RNA was purified using a Qiagen RNeasy protocol. To ensure intact RNA, samples were evaluated on an Agilent 2100 BioAnalyzer. Once RNA quality was assured, all specimens were analyzed labeling and hybridizings all RNAs to the U133 set described above and the raw data was analyzed The GeneExpress software package was used for analyzing the gene expression profiles.

Gene Expression Criteria for Choosing Candidates for Further Study

Genes that are ~3 to 10-fold or more elevated or repressed in melanoma cell lines and primary human melanomas by Affymetrix chip array data relative to primary human melanocytes or serial stages of melanoma progression were chosen for further analysis. This was following confirmation of the gene expression patterns of overexpressed or repressed gene candidates using RT-PCR on cDNAs from the primary melanomas, human melanocytes and melanoma cell lines evaluated.

Gene expression profiling studies on 10 melanoma cell lines derived from different stages of malignant progression were evaluated using Affymetrix microarray chips (U133 plus 2.0). Ten melanoma cell lines (3 cell lines with radial growth phase-like (RGP), 4 cell lines with vertical growth phase-like (VGP) phenotypes and 3 metastatic (MM) cell lines) were subjected to gene expression profile analysis. Extensive phenotypic characterizations of these cell lines included AJCC stage/pathology, level/thickness, mitotic rate, growth characteristics in soft agar, and growth factor dependency have been assessed[5]

Figure 1B:
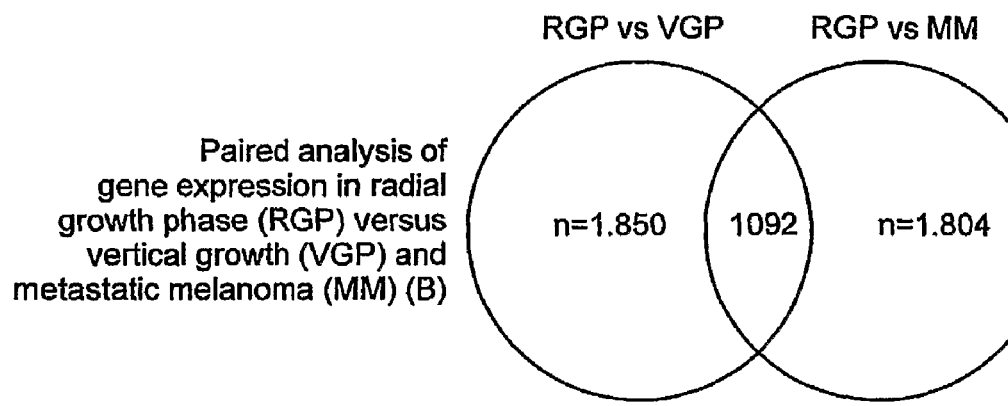
Figure 2:
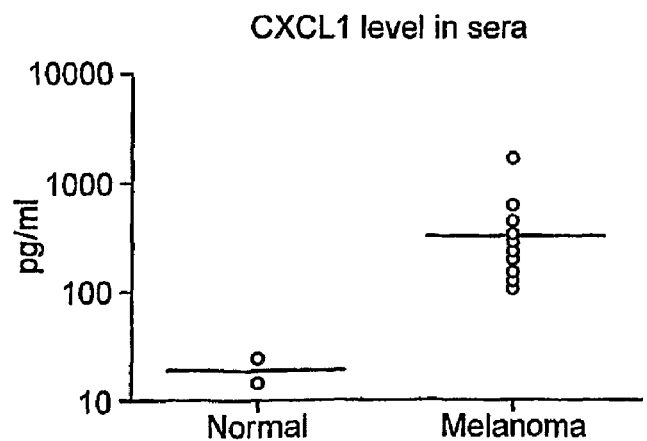
FIG. 2 depicts CXCL1 levels in the sera of normal and stage IV melanoma patients. ELISA analysis was performed using a GRO-α Quantikine Kit from R&D Systems Inc.

Unsupervised hierarchical clustering of the gene profiles of all cell lines was done. FIG. 1 depicts the results, including data demonstrating that the most similar global gene expression patterns are observed between VGP6 and MM9 as well as between VGP7 and MM10. Since those samples were serially derived from the same subjects (Pt A=VGP6/mm9, Pt B=VGP7/mm10), it is suggested that individual variation in gene profiling is a more decisive factor than disease stage variation in determining global gene expression patterns (FIG. 1A). It was also observed that RGP melanomas have distinctive gene expression profiles relative to VGP melanomas and MMs. This suggests that VGP and MM cell lines are more alike with regarding to their global gene expression patterns than their non-invasive predecessor lesions (FIG. 1A). The similarity of global gene expression pattern between VGP and MM samples relative to RGP also can be speculated from the paired analysis group matched samples (FIG. 1B). Approximately 60% of genes differentially expressed in VGP compared to RGP are also differentially expressed in MM (1,092 out of 1,850 genes and ESTs from VGP also differentially expressed in MM). Without wishing to be bound by any theory, this may indicate that melanoma progression from RGP to VGP requires more extensive genetic alterations than VGP to MM progression. In addition, the gene expression profile similarity between VGP and MM suggests that VGP melanomas may be fully equipped to become metastatic at the onset but require appropriate environmental cues for metastasis to occur.

Identification of genes required for the development of invasive melanoma aids in the identification of new diagnostic/prognostic melanoma markers. Several genes were identified that are specifically overexpressed (up-regulated) in VGP melanomas relative to RGP melanoma (VGP-specific genes). These genes are listed in Tables 1-2. Reduced levels (down-regulation) of the Markers listed in Table 3 were also identified. Several chemokines, including CXCL1, CXCL2 and CXCL8, which have recently been reported to be involved in cell migration, angiogenesis, tumor metastasis and immune responses, are among the genes most highly up-regulated in vertical growth phase melanomas, with the most up-regulated gene (>60-fold) being CXCL1 (also known as Melanoma Growth Stimulating Activity factor).

The invasion-specific genes identified in melanoma (Tables 1-3) may be used for, for example, diagnostic purposes, including, testing of secreted chemokine levels in subjects with melanoma will be evaluated for their utility as diagnostic/staging and/or prognostic markers. These can be achieved for example, with a rapid/simple ELISA antibody test, PCR methods, and/or mass spec analysis.

Also identified was MHC Class II antigens as upregulated in invasive melanomas and suspect this antigen may have prognostic significance for immune-mediated attack of tumor cells. These cell surface receptors are evaluated in tumor cells as prognostic markers and markers that may be used to predict response to immunotherapies in melanoma (e.g., vaccines, dendritic cell therapies, antibody-based therapies, and/or chemokine therapies).

Collection of Blood Samples

Exemplary method of obtaining peripheral blood samples include collecting blood with a large gauge needle (maximum gauge: 20). The tourniquet is removed once blood flow is established, and the initial 2 cc of collected blood is wasted. All blood samples are collected in serum separator tubes (SST) and allowed to clot at room temperature for one hour, to eliminate platelets. The samples then undergo a 10 minute centrifugation step at 1000×g to ensure platelet-poor plasma. The samples are then divided into aliquots and either tested with ELISA immediately or stored at <−20° C. until testing performed.

CXCL1 Assay

CXCL1 levels will be measured using a sandwiched enzyme-linked immunoabsorbent assay (ELISA), utilizing a commercially derived assay manufactured by R&D systems Inc (Minneapolis, Minn.). Measurements of CXCL1 serum levels are sensitive to CXCL1 released by platelet activation. In certain instances, concomitant measures of peripheral blood and central venous blood from untreated metastatic melanoma patients are evaluated to compare CXCL1 levels. All blood samples are collected in serum separator tubes (SST) and allowed to clot at room temperature in an effort to minimize platelet activation and release of CXCL1. As above, additional approaches to reduce platelet-derived CXCL1 include centrifugation at 1000×g for 10 minutes. Then the samples are divided into aliquots, and either evaluated with ELISA or stored at ≦−20° C. until testing performed.

A number of embodiments of the invention have been described. Nevertheless, it will be understood that various modifications may be made without departing from the spirit and scope of the invention. Accordingly, other embodiments are within the scope of the following claims.

REFERENCES

1. Hall, H. I., Miller, D. R., Rogers, J. D. & Bewerse, B. Update on the incidence and mortality from melanoma in the United States. *J Am Acad Dermatol* 40, 35-42. (1999).
2. Sondak, V. K. Adjuvant therapy for melanoma. *Cancer J7* Suppl 1, S24-7. (2001).
3. Bittner, M. et al. Molecular classification of cutaneous malignant melanoma by gene expression profiling. *Nature* 406, 536-40 (2000).
4. Su, Y. A. et al. Identification of tumor-suppressor genes using human melanoma cell lines UACC903, UACC903(+6), and SRS3 by comparison of expression profiles. *Mol Carcinog* 28, 119-27 (2000).
5. Satyamoorthy, K. et al. Melanoma cell lines from different stages of progression and their biological and molecular analyses. *Melanoma Res* 7 Suppl 2, S35-42 (1997).
6. Polsky, D., Young, A. Z., Busam, K. J. & Alani, R. M. The transcriptional repressor of p 16/Ink4a, Id1, is upregulated in early melanomas. *Cancer Res* 61, 6008-11 (2001).
7. Furuse, S. et al. Serum concentrations of the CXC chemokines interleukin 8 and growth-regulated oncogene-alpha are elevated in subjects with systemic sclerosis. *J Rheumatol* 30, 1524-8 (2003).

What is claimed is:

1. A product comprising isolated biomarkers bound to a biochip array, wherein the biomarkers are insulin-like growth factor binding protein 3, IL-6, and CXCL1.

2. The product of claim 1, wherein the biochip further comprises one or more biomarkers selected from the group consisting of Markers 78-104 that are down-regulated in a test sample obtained from a melanoma subject.

3. A product comprising purified biomarkers bound to a microarray comprising addressable locations using a biospecific capture reagent, wherein the biomarkers are insulin-like growth factor binding protein 3, IL-6, and CXCL1.

4. A kit for the diagnosis of melanoma, comprising:
purified biomarkers bound to a microarray comprising addressable locations using an adsorbent or capture reagent, wherein the purified biomarkers are insulin-like growth factor binding protein 3, IL-6, and CXCL1, and written instructions for
isolating a biomarker from a test sample comprising affected tissue isolated from a subject;
contacting the biomarker with the adsorbent or capture reagent such that the biomarker is retained;
detecting the differential presence of said biomarker in the test sample relative to a reference; and
correlating measurement of the biomarker with melanoma status.

5. A biochip array comprising isolated biomarkers, wherein the biomarkers are insulin-like growth factor binding protein 3, IL-6, and CXCL1.

6. A biochip array having addressable locations comprising isolated biomarkers, wherein the biomarkers are insulin-like growth factor binding protein 3, IL-6, and CXCL1.

7. A product comprising isolated biomarkers bound to a bead by a biospecific capture reagent, wherein the biomarkers are insulin-like growth factor binding protein 3, IL-6, and CXCL1.

8. The product of claim 7, wherein the biospecific capture reagent is an antibody.

9. A biochip comprising isolated biomarkers, wherein the biomarkers are insulin-like growth factor binding protein 3, IL-6, and CXCL1.

10. The biochip of claim 5, wherein the isolated biomarkers are present at addressable locations.

* * * * *